(12) United States Patent
Schoenfisch et al.

(10) Patent No.: US 9,850,322 B2
(45) Date of Patent: Dec. 26, 2017

(54) WATER SOLUBLE NITRIC OXIDE-RELEASING POLYGLUCOSAMINES AND USES THEREOF

(71) Applicant: The University of North Carolina at Chapel Hill, Chapel Hill, NC (US)

(72) Inventors: Mark Schoenfisch, Chapel Hill, NC (US); Yuan Lu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 24 days.

(21) Appl. No.: 14/421,525

(22) PCT Filed: Aug. 16, 2013

(86) PCT No.: PCT/US2013/055360
§ 371 (c)(1),
(2) Date: Feb. 13, 2015

(87) PCT Pub. No.: WO2014/028847
PCT Pub. Date: Feb. 20, 2014

(65) Prior Publication Data
US 2015/0225488 A1    Aug. 13, 2015

Related U.S. Application Data

(60) Provisional application No. 61/684,373, filed on Aug. 17, 2012.

(51) Int. Cl.
| | | |
|---|---|---|
| C08B 37/00 | (2006.01) |
| C08B 37/08 | (2006.01) |
| A61K 47/48 | (2006.01) |
| C08L 5/08 | (2006.01) |

(52) U.S. Cl.
CPC ...... C08B 37/003 (2013.01); A61K 47/48215 (2013.01); C08B 37/00 (2013.01); C08L 5/08 (2013.01)

(58) Field of Classification Search
None
See application file for complete search history.

(56) References Cited

U.S. PATENT DOCUMENTS

| | | | |
|---|---|---|---|
| 6,261,594 B1 * | 7/2001 | Smith | A61K 47/4823 424/422 |
| 6,451,337 B1 * | 9/2002 | Smith | A61K 47/4823 424/400 |
| 9,238,038 B2 | 1/2016 | Schoenfisch et al. | |
| 2005/0265956 A1 | 12/2005 | Liu et al. | |
| 2010/0305489 A1 | 12/2010 | Liu et al. | |
| 2011/0002999 A1 | 1/2011 | Chen et al. | |
| 2011/0150999 A1 | 6/2011 | Chu et al. | |

FOREIGN PATENT DOCUMENTS

| | | |
|---|---|---|
| JP | 2001-524991 A | 12/2001 |
| JP | 2002-518557 A | 6/2002 |
| WO | WO 2009/049208 A1 | 4/2009 |
| WO | WO 2012/046994 A2 | 4/2012 |

OTHER PUBLICATIONS

Gao, Q, et al., "Synthesis and Characterization of Chitosan-Based Diazeniumdiolates," Polymer *Materials Science and Engineering*, Dec. 2008, pp. 42-45, vol. 24(12).
Lu, Y., et al., "Nitric oxide-releasing chitosan oligosaccharides as antibacterial agents," *Biomaterials*, 2014, pp. 1716-1724, vol. 35, Elsevier Ltd.
Nichols, S., et al., "Local delivery of nitric oxide: Targeted delivery of therapeutics to bone and connective tissues," *Advanced Drug Delivery Reviews*, 2012, pp. 1177-1188, vol. 64, Elsevier B.V.
Wan, A., et al., "Characterization of folate-graft-chitosan as a scaffold for nitric oxide release," *International Journal of Biological Macromolecules*, 2008, pp. 415-421, vol. 43, Elsevier B.V.
Wan, A., et al., "Effects of Molecular Weight and Degree of Acetylation on the Release of Nitric Oxide from Chitosan—Nitric Oxide Adducts," *Journal of Applied Polymer Science*, 2010, pp. 2183-2188, vol. 117, Wiley Periodicals, Inc.

* cited by examiner

*Primary Examiner* — Traviss C McIntosh, III
(74) *Attorney, Agent, or Firm* — Alston & Bird LLP

(57) ABSTRACT

The presently disclosed subject matter provides nitric oxide-releasing polysaccharides and oligosaccharides, in particular, polyglucosamines, and their use in biomedical and pharmaceutical applications. More particularly, in some embodiments, the presently disclosed subject matter provides nitric oxide-releasing polysaccharides and oligosaccharides that release nitric oxide in a controlled and targeted manner, thereby prolonging the therapeutic effects of nitric oxide and improving the specificity of nitric oxide delivery to targeted cells and/or tissues.

37 Claims, 10 Drawing Sheets

|  | As NO-releasing scaffolds | Penetration of biofilms |
|---|---|---|
| Chitosan | Low storage (~0.2 µmol/mg) due to insolubility under basic conditions. | No |
| Chitosan oligosaccharides | Higher storage expected due to solubility under basic conditions. | Yes |

Fig. 1

|  | C (%) | H (%) | N (%) |
|---|---|---|---|
| Chitosan oligosaccharides | 42.2 ± 1.6 | 6.8 ± 0.1 | 6.3 ± 0.2 |
| CSO 1 | 43.5 ± 1.2 | 7.7 ± 0.3 | 8.9 ± 0.1 |
| CSO 2 | 44.7 ± 1.8 | 8.4 ± 0.2 | 10.8 ± 0.8 |
| CSO 3 | 51.0 ± 0.2 | 9.0 ± 0.2 | 3.1 ± 0.1 |

|  | t[NO] (μmol/mg) | [NO]$_{max}$ (ppb/mg) | t$_{1/2}$ (h) |
|---|---|---|---|
| CSO 1-NO | 0.30 ± 0.04 | 1600 ± 215 | 3.60 ± 0.13 |
| CSO 2-NO | 0.87 ± 0.16 | 5500 ± 414 | 2.20 ± 0.14 |
| CSO 3-NO | 0.35 ± 0.02 | 12600 ± 2121 | 0.15 ± 0.01 |

WATER SOLUBLE NITRIC OXIDE-RELEASING POLYGLUCOSAMINES AND USES THEREOF

GOVERNMENT INTEREST

This invention was made with government support under EB000708 awarded by The National Institutes of Health. The Government has certain rights in the invention.

FIELD OF THE INVENTION

The presently disclosed subject matter provides nitric oxide-releasing polysaccharides and oligosaccharides, in particular, polyglucosamines, and their use in biomedical and pharmaceutical applications. More particularly, in some embodiments, the presently disclosed subject matter provides nitric oxide-releasing oligosaccharides that release nitric oxide in a controlled and targeted manner, thereby prolonging the therapeutic effects of nitric oxide and improving the specificity of nitric oxide delivery to targeted cells and/or tissues.

BACKGROUND OF THE INVENTION

The discovery of the multifaceted role of nitric oxide (NO) in biology, physiology, and pathophysiology, see Marietta, M. A., et al., *BioFactors*, 2, 219-225 (1990), has led to the search for nitric oxide donors capable of controlled nitric oxide release. See Keefer, L. K., *Chemtech*, 28, 30-35 (1998). To date, researchers have discovered that NO regulates a range of biological processes in the cardiovascular, gastrointestinal, genitourinary, respiratory, and central and peripheral nervous systems. See Ignarro, L. J., *Nitric Oxide: Biology and Pathobiology*; Academic Press: San Diego, 2000; and Ignarro, L. J. et al., *Proc. Natl. Acad. Sci.*, USA., 84, 9265-9269 (1987). Furthermore, the discovery of NO as a vasodilator and its identification as both an antibiotic and a tumoricidal factor have made NO an attractive pharmaceutical candidate. See, for example, Radomski, M. W., et al., *Br. J. Pharmacol.*, 92, 639-646 (1987); Albina, J. E., and Reichner, J. S.; *Canc. Metas. Rev.*, 17, 19-53 (1998); Nablo, B. J., at al., *J. Am. Chem. Soc.*, 123, 9712-9713 (2001); Cobbs, C. S., et al., *Cancer Res.*, 55, 727-730 (1995); Jenkins, D. C., at al., *Proc. Natl. Acad. Sci., USA.*, 92, 4392-4396 (1995); and Thomsen, L. L., et al., *Br. J. Cancer.*, 72, 41-44 (1995).

Several nitric oxide donors have been reported, the most notable being N-diazeniumdiolates. Generally, N-diazeniumdiolate NO donors are small molecules synthesized by the reaction of amines with NO at elevated pressure and have been used, for example, to spontaneously generate NO in aqueous solution. See Hrabie, J. A. and Keefer, L. K., *Chem. Rev.*, 102, 1135-1154 (2002).

Therapeutic strategies to explore the activities of nitric oxide donors, for example, to kill tumor cells, are problematic in part because the nitric oxide delivery systems known in the art release or donate nitric oxide indiscriminately. Thus, there is a need in the art for a nitric oxide delivery system that releases or donates nitric oxide in a controlled and/or targeted manner to facilitate an improved understanding of the function of NO in physiology and to provide for the development of NO-associated therapies.

SUMMARY OF THE INVENTION

In embodiments, the subject matter disclosed herein is directed to a polyglucosamine that contains a covalently bound nitric oxide releasing moiety, i.e. a NO donor. At least one structural unit in the polyglucosamine backbone contains the structural unit of formula I. Optionally, at least one structural unit of the polyglucosamine further comprises the structural unit of formula II. Advantageously, the polyglucosamine described herein is water soluble and is capable of delivering NO to a target.

In embodiments, the subject matter disclosed herein is directed to methods of delivering or releasing NO to a subject comprising administering a polyglucosamine comprising at least one structural unit of formula I and optionally, further comprising at least one structural unit of formula II.

In embodiments, the subject matter disclosed herein is directed to methods of treating a disease state in a subject comprising administering a polyglucosamine comprising at least one structural unit of formula I and optionally, further comprising at least one structural unit of formula II.

In embodiments, the subject matter disclosed herein is directed to a pharmaceutical composition comprising a polyglucosamine containing at least one structural unit of formula I and optionally, further comprising at least one structural unit of formula II and a pharmaceutically acceptable carrier, excipient or diluent.

In embodiments, the subject matter disclosed herein is directed to methods of preparing a polyglucosamine comprising at least one structural unit of formula I and optionally, further comprising at least one structural unit of formula II.

In another embodiment, the subject matter disclosed herein is directed to a method of disrupting, eradicating or preventing a biofilm by employing a polyglucosamine comprising at least one structural unit of formula I and optionally, further comprising at least one structural unit of formula II.

The subject matter is described fully in the drawings herein and in the specification set forth below.

BRIEF DESCRIPTION OF THE FIGURES

FIG. 1 describes an advantageous property of the presently disclosed functionalized polyglucosamines.

FIG. 2 shows the percent of C, H and N found in certain embodiments.

FIG. 6 shows the t[NO], [NO]$_{max}$, and $t_{1/2}$ of certain embodiments.

DETAILED DESCRIPTION

Figure 3:
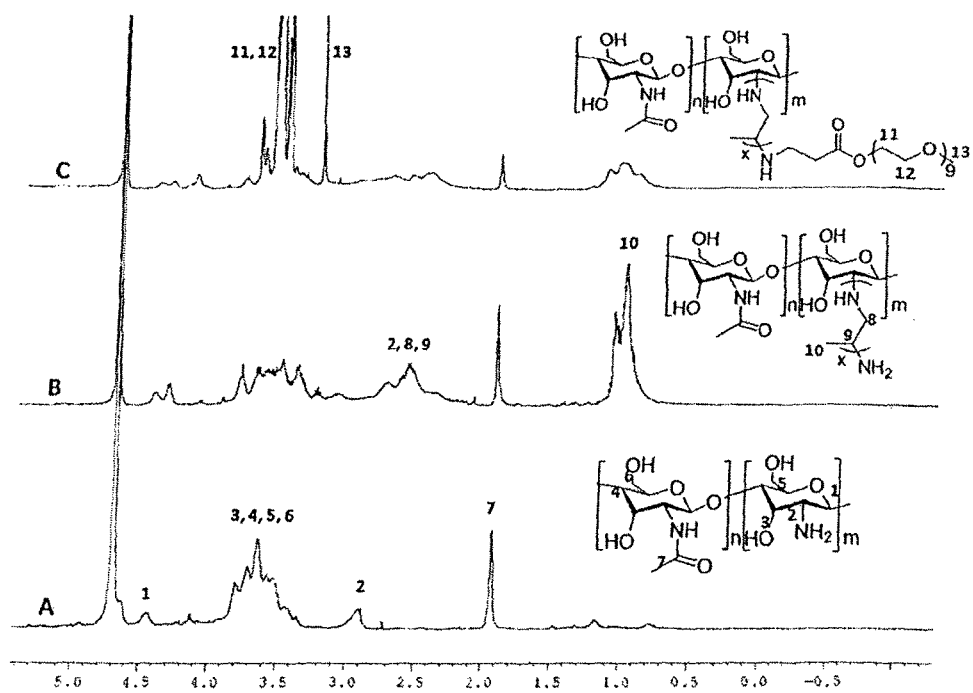
FIG. 3 is a $^1$H NMR of certain embodiments.

The presently disclosed nitric oxide (NO) releasing polyglucosamines, also referred to in embodiments as NO-releasing chitosan oligosaccharides, are advantageously water soluble and tunable. These properties contribute to the usefulness of the presently disclosed polyglucosamines in therapeutics and disease states where water soluble therapeutics are advantageous, for example, in the treatment of cystic fibrosis. Other advantages over known NO releasing particles that the presently disclosed functionalized NO releasing polyglucosamines possess include: 1. Distinct synthesis routes and chemical composition by grafting secondary amine-containing oligomer chains onto chitosan oligosaccharides; 2. Tunability of NO storage and NO-release kinetics is an advantage. By tuning the number of secondary amines on the aziridine oligomer side chains, NO storage can be controlled. Further functionalization of the amines on the resulting materials by compounds of different hydrophobicity/hydrophilicity enables the control over NO-release kinetics. Indeed, much larger NO storage was yielded by the presently disclosed functionalized polyglucosamines; and 3. In contrast to particles, the functionalized polyglucosamines described herein are water soluble, facilitating a wider range of applications including biomedical application where water-solubility is desired. A previously disclosed NO-releasing chitosan (U.S. Pat. No. 6,451,337) is not water soluble. This highlights another advantage that the presently disclosed water soluble functionalized can readily penetrate and eradicate biofilms.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" NO releasing moiety can mean a single or a multiplicity.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition.

The term "treatment effective amount" or "effective amount," as used herein, refers to that amount of a functionalized polyglucosamine that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

The terms "disrupting" and "eradicating" refer to the ability of the presently disclosed functionalized polyglucosamines to combat biofilms. The biofilms may be partially eradicated or disrupted, meaning that the cells no longer attach to one another or to a surface. The biofilm may be completely eradicated, meaning that the biofilm is no longer an interconnected, cohesive or continuous network of cells to a substantial degree.

As used herein, the term "water soluble" means that the functionalized polyglucosamine is more soluble in water at room temperature than the polyglucosamine before functionalization. Preferably, water soluble functionalized polyglucosamines disclosed herein are soluble such that >50 mg of functionalized polyglucosamine dissolves per mL of water. More preferably, water soluble functionalized polyglucosamines disclosed herein are soluble such that >75 mg of functionalized polyglucosamine dissolves per mL of water. Most preferably, water soluble functionalized polyglucosamines disclosed herein are soluble such that >100 mg of functionalized polyglucosamine dissolves per mL of water.

The terms "nitric oxide donor" or "NO donor" refer to species that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The terms "nitric oxide releasing" or "nitric oxide donating" refer to methods of donating, releasing and/or directly or indirectly transferring any of the three redox forms of nitrogen monoxide (NO+, NO−, NO). In some cases, the nitric oxide releasing or donating is accomplished such that the biological activity of the nitrogen monoxide species is expressed at the intended site of action.

The term "microbial infection" as used herein refers to bacterial, fungal, viral, and yeast infections.

The "patient" or "subject" treated in the many embodiments disclosed herein is desirably a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The present invention finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

The subject can be a subject "in need of" the methods disclosed herein can be a subject that is experiencing a disease state and/or is anticipated to experience a disease state, and the methods and compositions of the invention are used for therapeutic and/or prophylactic treatment.

The oligosaccharide described herein are polyglucosamines. Polyglucosamines and derivatives thereof are known in the as chitosans and derivatives thereof. Particularly useful polyglucosamines are polymers that can range in size 100 to 20,000 g/mol. Smaller polyglucosamines having molecular weights below 100 g/mol and larger ones having molecular weights above 20,000 g/mol are also contemplated. Chitosans having a molecular weight above 20,000 g/mol may need to be further functionalized to be water soluble. An important feature of useful polyglucosamines is an available nitrogen on the carbohydrate backbone that is derivatized according to the methods described herein to form a NO-releasing polyglucosamine. Advantageously, the polyglucosamines disclosed herein are water soluble.

Chitosan is a linear polysaccharide composed of randomly distributed β-(1-4)-linked D-glucosamine (deacetylated unit) and N-acetyl-D-glucosamine (acetylated unit). It is a polyglucosamine. Chitosan is derived from chitin, a polysaccharide found in the exoskeleton of shellfish such as shrimp, lobster, and or crabs. It has the following structure:

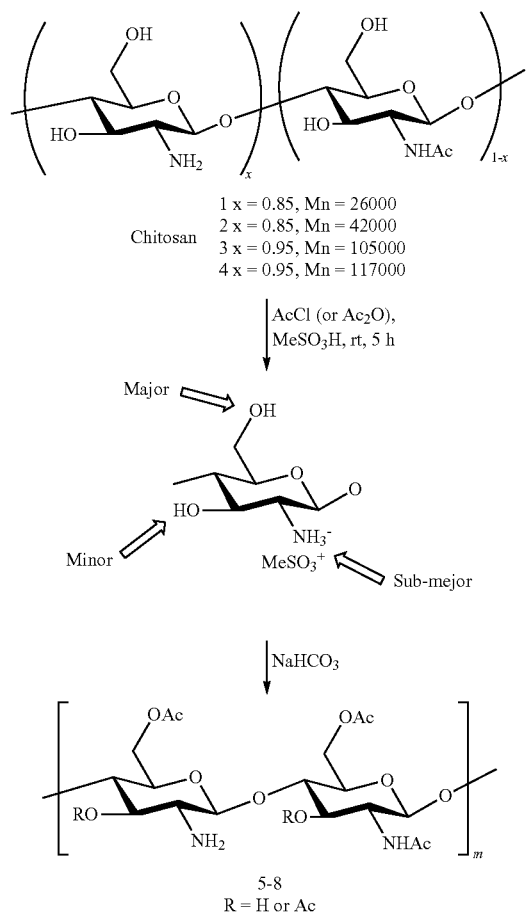

Chitosan is biodegradable and biocompatible. Chitosan itself is only soluble under acidic conditions. Chitosan polysaccharides are insoluble under physiological conditions. Additionally, their NO storage is rather modest (~0.2 µmol/mg) likely due to poor solubility of polysaccharides in basic solutions necessary for NO donor formation. Valmikinathan, C. M.; Mukhatyar, V. J.; Jain, A.; Karumbaiah, L.; Dasari, M.; Bellamkonda, R. V. Photocrosslinkable chitosan based hydrogels for neural tissue engineering. *Soft Matter* 2012, 8, 1964-1976; Zhang, J. L.; Xia, W. S.; Liu, P.; Cheng, Q. Y.; Tahirou, T.; Gu, W. X.; Li, B. Chitosan Modification and Pharmaceutical/Biomedical Applications. *Mar. Drugs* 2010, 8, 1962-1987; Wan, A.; Gao, Q.; Li, H. L. Effects of molecular weight and degree of acetylation on the release of nitric oxide from chitosan-nitric oxide adducts. *J. Appl. Polym. Sci.* 2010, 117, 2183-2188. To synthesize N-diazeniumdiolate-functionalized chitosan derivatives with improved NO storage, we prepared water-soluble chitosan oligosaccharides by the degradation of chitosan polysaccharides in hydrogen peroxide. A benefit of the chitosan oligosaccharides described herein are relatively low-molecular weight from 100 to 20,000 g/mol, in particular about 10,000 g/mol or less; or about 8000 g/mol or less; or about 5000 g/mol or less; or about 2,500 g/mol or less and their ability to readily penetrate biofilms. Maghami, G. G.; Roberts, G. A. F. Evaluation of the viscometric constants for chitosan. *Makromol. Chem.* 1988, 189, 195-200; Porporatto, C.; Bianco, I. D.; Riera, C. M.; Correa, S. G., Chitosan induces different L-arginine metabolic pathways in resting and inflammatory macrophages. *Biochem. Biophy. Res. Comm.*

2003, 304, 266-272. Chitosan oligosaccharides described herein have greater NO storage of up to about 8.7 μmol/mg and are also soluble under neutral and basic conditions.

The primary amino groups on the backbone of chitosan are chemical handles for the preparation of the NO-releasing oligosaccharides disclosed herein. As shown in the schemes below, secondary amino groups are prepared from the primary amino groups.

Useful agents to form the secondary amino groups are selected from the group consisting of aziridines, in particular 2-methyl aziridine, and thiiranes and the like.

In an embodiment, the subject matter disclosed herein is directed to a polyglucosamine, e.g., a chitosan oligosaccharide comprising at least one structural unit of formula I:

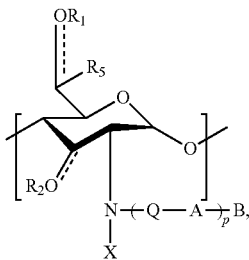

and optionally, at least one structural unit of formula II:

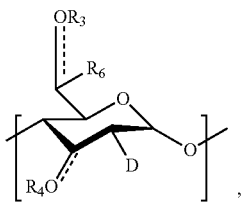

wherein, $R_1$, $R_2$, $R_3$ and $R_4$, if present, are each independently selected from the group consisting of hydrogen; $C_{1-5}$ alkyl(C=O)—, when the $C_{1-5}$ alkyl is methyl, Me(C=O)— is an acyl, Ac; and $C_{1-5}$ alkyl;

----, in each instance, is a single or double bond, wherein in each instance where it is a double bond, $R_1$, $R_2$, $R_3$ or $R_4$ attached to the double bond-O is absent; when $R_1$ is absent, $R_5$ is hydrogen, hydroxyl, $C_{1-5}$ alkyl or $C_{1-5}$ alkoxy; when $R_3$ is absent, $R_6$ is hydrogen, hydroxyl, $C_{1-5}$ alkyl or $C_{1-5}$ alkoxy;

wherein in each instance where it is a single bond, $R_1$, $R_2$, $R_3$ or $R_4$ attached to the double bond-O is present; when $R_1$ is present, $R_5$ is hydrogen; when $R_3$ is present, $R_6$ is hydrogen;

Q is —$(CR_cR_d)_v$—;

wherein $R_c$ and $R_d$ are independently hydrogen or $C_{1-5}$ alkyl, such as methyl, ethyl, n-propyl, isopropyl, t-butyl, n-butyl, isobutyl and pentyl.

Preferably, $R_c$ and $R_d$ are independently hydrogen, methyl or ethyl; and v is an integer from 2 to 6; preferably, v is 2;

p is an integer from 1 to 100, preferably 1 to 50; more preferably 1 to 25; most preferably 1 to 10;

A is

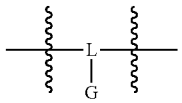

wherein, L is S, O or N; and

G, in each instance, is independently, hydrogen, or is taken together with L to form a nitric oxide donor;

X is hydrogen, $C_{1-5}$ alkyl or is taken together with N to form a nitric oxide donor;

B is hydrogen or —Y—Z, wherein Y is a spacer and Z is a polymer or a terminus group; or B is absent;

D is —$NR_aR_b$, wherein $R_a$ and $R_b$ are independently selected from the group consisting of hydrogen, formyl, $C_{1-5}$ alkyl(C=O)—, when the $C_{1-5}$ alkyl is methyl, Me(C=O)— is an acyl, Ac, $C_{1-5}$ alkyl and $C_{1-5}$ alkyl ester;

or D is

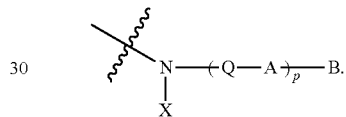

Useful values of $R_1$, $R_2$, $R_3$ and $R_4$, if present, are each independently selected from the group consisting of hydrogen and $C_{1-5}$ alkyl. When one or more of $R_1$, $R_2$, $R_3$ and $R_4$ is $C_{1-5}$ alkyl, it is selected from methyl, ethyl, n-propyl, isopropryl, t-butyl, n-butyl, isobutyl and pentyl. Preferably, $R_1$, $R_2$, $R_3$ and $R_4$, if present, is hydrogen or methyl. Most preferably, $R_1$, $R_2$, $R_3$ and $R_4$, if present, is hydrogen.

In all embodiments, ----, in each instance, is a single or double bond. Preferably, it is a single bond in all instances.

Q is —$(CR_cR_d)_v$—; wherein $R_c$ and $R_d$ are independently hydrogen or $C_{1-5}$ alkyl, such as methyl, ethyl, n-propyl, isopropryl, t-butyl, n-butyl, isobutyl and pentyl. Preferably, $R_c$ and $R_d$ are independently hydrogen, methyl or ethyl. Useful values of v are integers from 2 to 6. Preferably, v is 2.

Useful values of p include any integer from 1 to 100. Preferably p is an integer from 1 to 50. More preferably, p is an integer from 1 to 25. Most preferably, p is an integer from 1 to 10, such as, 1, 2, 3, 4, 5, 6, 7, 8, 9 and 10.

Useful values of L are N, S and O. Preferably, L is N or S. In each instance that G occurs, it is independently hydrogen or a nitric oxide donor. Since the nitric oxide donor contributes to the amount of available NO on the polyglucosamine, it is preferable that G is a nitric oxide donor. In preferred embodiments, at least 30% of G present on a polyglucosamine is a nitric oxide donor. More preferably, at least 50% of G present on a polyglucosamine is a nitric oxide donor. Even more preferably, at least 90% of G present on a polyglucosamine is a nitric oxide donor. Most preferably, at least 95% of G present on a polyglucosamine is a nitric oxide donor.

Useful values of X are hydrogen, $C_{1-5}$ alkyl or a nitric oxide donor. Since the nitric oxide donor contributes to the amount of available NO on the polyglucosamine, it is preferable that X is a nitric oxide donor. In preferred embodiments, at least 30% of X present on a polyglucosamine is a nitric oxide donor. More preferably, at least 50% of X present on a polyglucosamine is a nitric oxide donor. Even more preferably, at least 90% of X present on a polyglucosamine is a nitric oxide donor. Most preferably, at least 95% of X present on a polyglucosamine is a nitric oxide donor.

Useful values of B are hydrogen, —Y—Z, wherein Y is a spacer and Z is a monomer or polymer, or B is a terminus group. B may also be absent when L is O or S. As used herein, a terminus group is any end-capping group at the terminus of a polymer or monomer. These groups are known in the art. Preferably, when B is a terminus group, it is hydrogen, hydroxyl or $C_{1-5}$ alkyl.

Useful values of Z include monomers and polymers known in the art, especially those used in active pharmaceutical ingredients. Particularly useful polymers or monomers include:

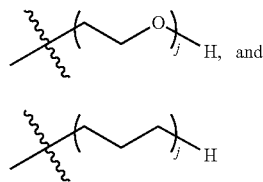

wherein j, in each instance, is an integer from 1 to 100.

Useful spacers, Y, in the formulae disclosed herein include spacers or linkers known in the art, especially those used in active pharmaceutical ingredients. Particularly useful spacers include the following:

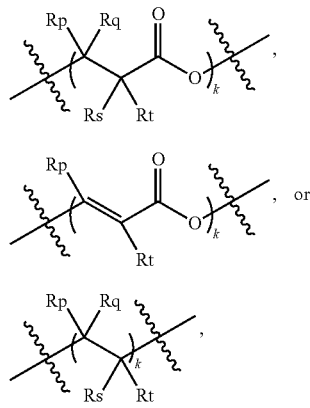

wherein, $R_p$, $R_q$, $R_s$ and $R_t$, in each instance, are independently, hydrogen or hydroxyl; and k is an integer from 1 to 20.

Using the strategies disclosed herein, any secondary amino group present on the oligosaccharide can be modified as described herein to form a NO-releasing oligosaccharide. The secondary amino groups attached directly to the sugar backbone moieties or secondary amino groups pendant on the backbone sugar moieties can be functionalized with a NO releasing moiety. As disclosed fully herein in the synthetic routes, primary amines are modified to secondary amines. This modification can be facilitated by aziridines, thiiranes and the like.

Useful NO releasing moieties include any NO releasing group known in the art. Particularly useful are residues of NO releasing groups, i.e. NO donors, are covalently bound to N, S or O on the polyglucosamine. The NO donor is taken together with the atom on the polyglucosamine to which it is bound to form a moiety selected from the group consisting of a diazeniumdiolate, —NO as part of a nitrosothiol group for example, a nitrosamine, a hydroxyl nitrosamine, a hydroxyl amine, a hydroxyurea, and combination thereof. Preferably, the NO releasing moiety is a diazeniumdiolate. These groups may be present in the form of a salt.

In some embodiments, the NO donor is a N-diazeniumdiolate (i.e., a 1-amino-substituted deazen-1-lum-1,2-diolate), N-Diazeniumdiolates are particularly attractive as NO donors due to their ability to generate NO spontaneously under biological conditions. See Hrabie, J. A. and Keefer, L. K., *Chem. Rev.*, 102, 1135-1154 (2002); and Napoli, C. and Ianarro, L. J., *Annu. Rev. Pharmacol. Toxicol.*, 43, 97-123 (2003). Several N-diazeniumdiolate compounds have been synthesized using a range of nucleophilic residues that encompass primary and secondary amines, polyamines, and secondary amino acids, See Hrabie, J. A., and Keefer L. K., *Chem. Rev.*, 102, 1135-1154 (2002). In the formation of the N-diazeniumdiolate, one equivalent of amine reacts with two equivalents of nitric oxide under elevated pressure. A base (e.g., an alkoxide like methoxide) removes a proton from the amine nitrogen to create the anionic, stabilized [N(O)NO] group. While stable under ambient conditions, N-diazeniumdiolates decompose spontaneously in aqueous media to generate NO at rates dependent upon pH, temperature, and/or the structure of the amine moiety. For example, N-diazeniumdiolate-modified proline (PROLI/NO), 2-(dimethylamino)-ethylputreamlne (DMAEP/NO), N,N-dimethylhexanediamine (DMHD/NO), and diethylenetriamine (DETA/NO) have been developed as small molecule NO donors with diverse NO release half-lives ranging from 2 seconds to 20 hours at pH 7.4 and 37° C. See Hrabie, J. A., and Keefer, L. K., *Chem. Rev.*, 102, 1135-1154 (2002); and Keefer, L. K., *Annu, Rev. Pharmacol. Toxicol* 43, 585-607 (2003).

The secondary amine functional group of the polyglucosamine is converted in high yields to a nitric oxide donor in the presence of a strong base and gaseous nitric oxide. As provided herein, the solvent system can affect the charging of the polyglucosamine with NO.

In an embodiment, when the polyglucosamine is specifically functionalized with an aziridine as described herein, the functionalized polyglucosamine comprises at least one structural unit of formula Ia:

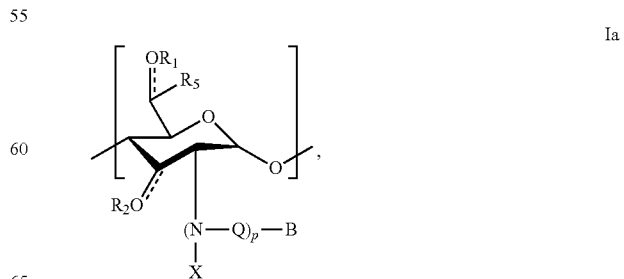

and optionally, at least one structural unit of formula IIa:

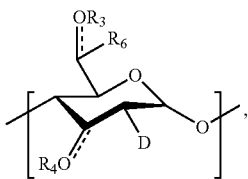

IIa wherein, the definitions of the variables are as defined above with the exception of D. In this embodiment, D is —$NR_aR_b$, wherein $R_a$ and $R_b$ are independently selected from the group consisting of hydrogen, formyl, $C_{1-5}$ alkyl(C=O)—, $C_{1-5}$ alkyl and $C_{1-5}$ alkyl ester; or D has the structure:

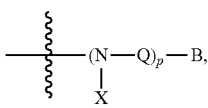

wherein, X, Q, p and B are as described above.

In an aspect of this embodiment, when the polyglucosamine is specifically functionalized with an aziridine as described herein, the functionalized polyglucosamine comprises at least one structural unit of formula VIII:

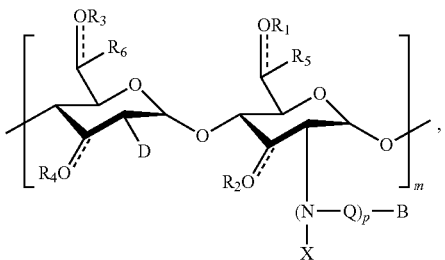

VIII wherein, the variables are as described above for this embodiment.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

The terms "cationic amine" and "quaternary amine" refer to an amino group having an additional (i.e., a fourth) group, for example a hydrogen or an alkyl group bonded to the nitrogen. Thus, cationic and quaternary amines carry a positive charge.

The term "alkyl" denotes a straight or branched hydrocarbon chain containing 1-24 carbon atoms, e.g., 1-12 carbon atoms. Examples of alkyl group include methyl, ethyl, propyl, isopropyl, butyl, isobutyl, tert-butyl, and the like.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 5 carbon atoms in length, more preferably 1-3 carbon atoms in length.

The following specific embodiments are disclosed:

1. A polyglucosamine (chitosan oligosaccharide) comprising, at least one structural unit:

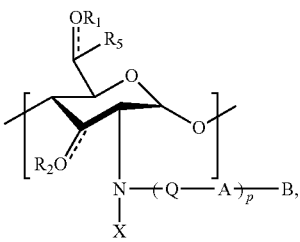

I and optionally, at least one structural unit:

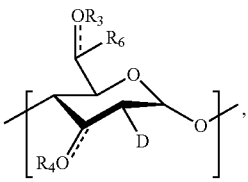

II wherein, $R_1$, $R_2$, $R_3$ and $R_4$, if present, are each independently selected from the group consisting of hydrogen, $C_{1-5}$ alkyl(C=O)— and $C_{1-5}$ alkyl;

- - - - , in each instance, is a single or double bond, wherein in each instance where it is a double bond, $R_1$, $R_2$, $R_3$ or $R_4$ attached to the double bond-O is absent; when $R_1$ is absent, $R_5$ is hydrogen, hydroxyl, $C_{1-5}$ alkyl or $C_{1-5}$ alkoxy; when $R_3$ is absent, $R_6$ is hydrogen, hydroxyl, $C_{1-5}$ alkyl or $C_{1-5}$ alkoxy;

wherein in each instance where it is a single bond, $R_1$, $R_2$, $R_3$ or $R_4$ attached to the double bond-O is present; when $R_1$ is present, $R_5$ is hydrogen; when $R_3$ is present, $R_6$ is hydrogen;

Q is —$(CR_cR_d)_v$—;

wherein $R_c$ and $R_d$ are independently hydrogen or $C_{1-5}$ alkyl; and v is an integer from 2 to 6;

p is an integer from 1 to 10;

A is

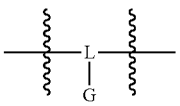

wherein, L is S, O or N; and

G, in each instance, is independently, hydrogen, or is taken together with L to form a nitric oxide donor or is absent;

X is hydrogen, $C_{1-5}$ alkyl or is taken together with N to form a nitric oxide donor;

B is one hydrogen or —Y—Z, wherein Y is a spacer and Z is a polymer or a terminus;

D is —$NR_aR_b$, wherein $R_a$ and $R_b$ are independently selected from the group consisting of hydrogen, formyl, $C_{1-5}$ alkyl(C=O)—, $C_{1-5}$ alkyl and $C_{1-5}$ alkyl ester;

or D is

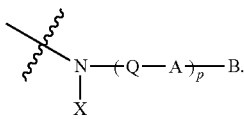

2. The polyglucosamine of embodiment 1, wherein at least one of the X and G is taken together with the atom on the polyglucosamine to which it is bound to form a nitric oxide donor.
3. The polygucosamine of embodiment 1, comprising the structural unit: 4.

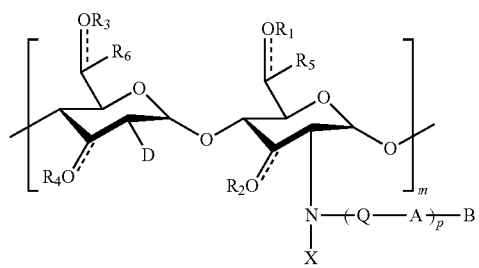

III wherein,
m is an integer from 1 to 10,000.
5. The polyglucosamine of embodiment 1, wherein the nitric oxide donor is taken together with the atom on the polyglucosamine to which it is bound is selected from the group consisting of a diazeniumdiolate, nitrosothiol, a nitrosamine, a hydroxyl nitrosamine, a hydroxyl amine, a hydroxyurea, and combination thereof.
5. The polyglucosamine of embodiment 4, wherein the nitric oxide donor is diazeniumdiolate.
6. The polyglucosamine of embodiment 3, wherein m is an integer from 1 to 50.
7. The polyglucosamine of embodiment 3, wherein m is an integer from 1 to 10.
8. The polyglucosamine of embodiment 1, comprising at least one structural unit:

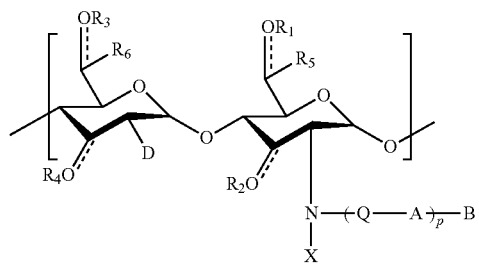

IV wherein,
D is —$NR_aR_b$, wherein $R_a$ and $R_b$ are independently selected from the group consisting of hydrogen, formyl, $C_{1-5}$ alkyl(C=O)—, $C_{1-5}$ alkyl and $C_{1-5}$ alkyl ester.

9. The polyglucosamine of embodiment 8, wherein
‑ ‑ ‑ ‑ in each instance, is a single bond
$R_1$, $R_2$, $R_3$ and $R_4$, are each hydrogen, and
$R_5$ and $R_6$ are each hydrogen.
10. The polyglucosamine of embodiment 9, comprising at least one structural unit:

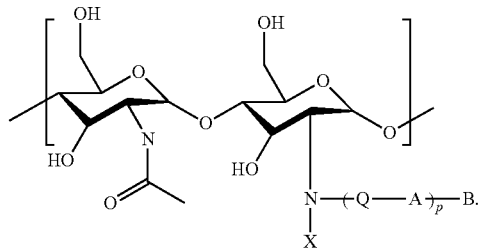

V

11. The polyglucosamine of embodiment 10, wherein B is hydrogen.
12. The polyglucosamine of embodiment 11, wherein B is —Y—Z.
13. The polyglucosamine of embodiment 12, wherein B is —Y—Z, wherein Z has the structure:

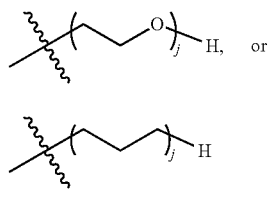

i or ii wherein j, in each instance, is an integer from 1 to 100.
14. The polyglucosamine of embodiment 12, wherein Y has the structure:

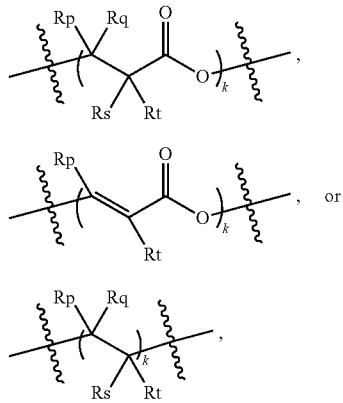

iii iv

, or v wherein,
$R_p$, $R_q$, $R_s$ and $R_t$, in each instance, are independently, hydrogen or hydroxyl; and
k is an integer from 1 to 20.

15. The polyglucosamine of embodiment 1, comprising the structural unit:

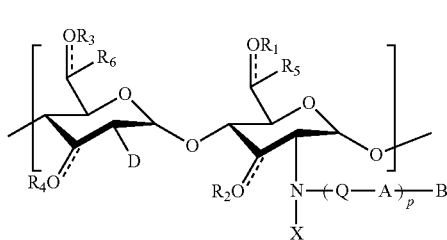

IV wherein,
D is

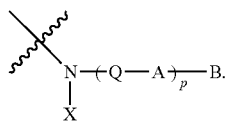

16. The polyglucosamine of embodiment 15, wherein
    ---- in each instance, is a single bond, and
    $R_1$, $R_2$, $R_3$ and $R_4$, are each hydrogen.
17. The polyglucosamine of embodiment 1, wherein
    B is —Y—Z, wherein Z has the structure:

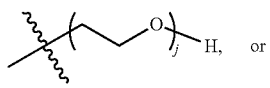

wherein j, in each instance, is an integer from 1 to 100.
18. The polyglucosamine of embodiment 17, wherein j is an integer from 1 to 50.
19. The polyglucosamine of embodiment 17, wherein j is an integer from 1 to 15.
20. The polyglucosamine of embodiment 1, wherein

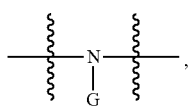

wherein G is hydrogen, or is taken together with N to form a nitric oxide donor or is absent; and B is hydrogen.

21. The polyglucosamine of embodiment 1, comprising the structural unit:

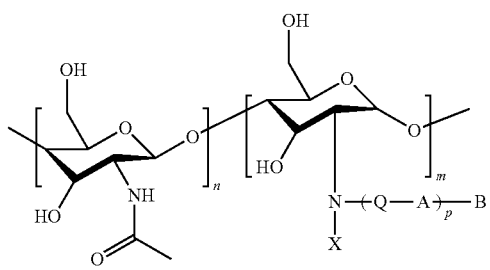

VI wherein,
m is an integer from 1 to 1,000, and
n is an integer from 1 to 1,000.
22. The polyglucosamine of embodiment 21, wherein m and n are each independently selected from an integer of 1 to 50.
23. The polyglucosamine of embodiment 21, comprising the structural unit: 24.

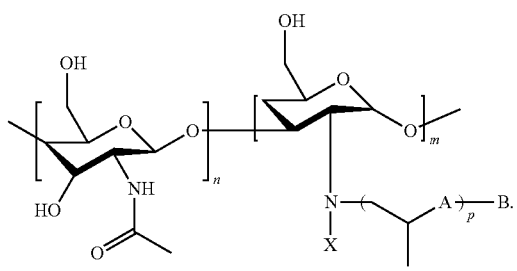

VII

25. The polyglucosamine of embodiment 20, wherein
    X is hydrogen or is taken together with N to form a diazeniumdiolate; and
    A is

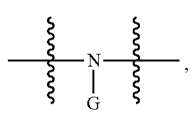

wherein G is hydrogen or is taken together with N to form a diazeniumdiolate.
26. The polyglucosamine of embodiment 21, wherein
    B is —Y—Z, wherein Z has the structure:

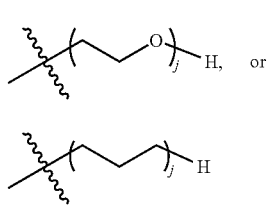

wherein j, in each instance, is an integer from 1 to 100.

27. The polyglucosamine of embodiment 22, wherein Y has the structure:

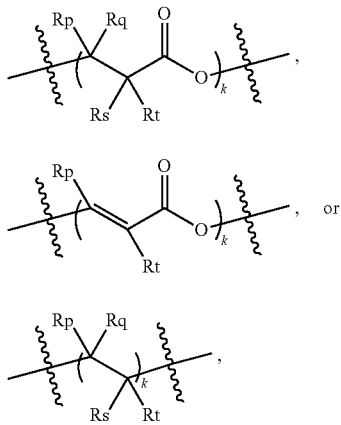

wherein, $R_p$, $R_q$, $R_s$ and $R_t$, in each instance, are independently, hydrogen or hydroxyl; and k is an integer from 1 to 20.

29. The polyglucosamine of embodiment 1, wherein A is N.

30. The polyglucosamine of embodiment 1, wherein A is S.

31. The polyglucosamine of embodiment 1, wherein $R_c$ and $R_d$ are independently hydrogen or methyl; and v is 2.

32. A method of delivering nitric oxide to a subject, comprising:
   administering an effective amount of the polyglucosamine of claim 1 to the subject.

33. A method of treating a disease state, comprising:
   administering an effective amount of the polyglucosamine of embodiment 1 to a subject in need thereof, wherein the disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

34. The method of embodiment 31, wherein said disease state is cystic fibrosis.

35. A pharmaceutical formulation comprising:
   i. the polyglucosamine of claim 1; and
   ii. a pharmaceutically acceptable carrier.

36. The pharmaceutical formulation of embodiment 33, wherein the polyglucosamine is water-soluble.

35. The polyglucosamine of embodiment 1, wherein the polyglucosamine is water soluble.

In all embodiments, combinations of substituents and/or variables are permissible only if such combinations result in compounds that conform to a known valence for each atom.

Specific functionalized polyglucosamines include:

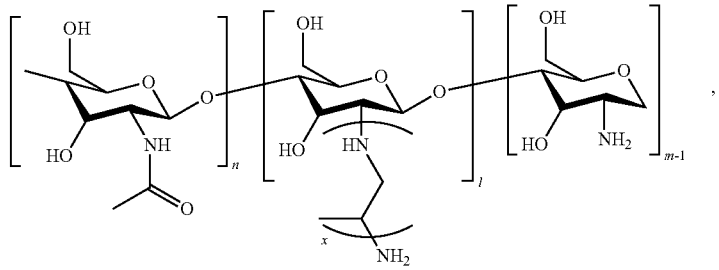

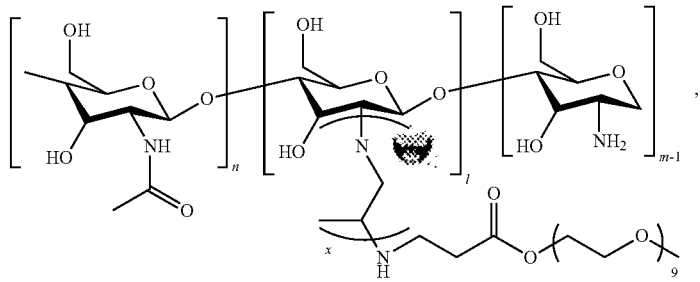

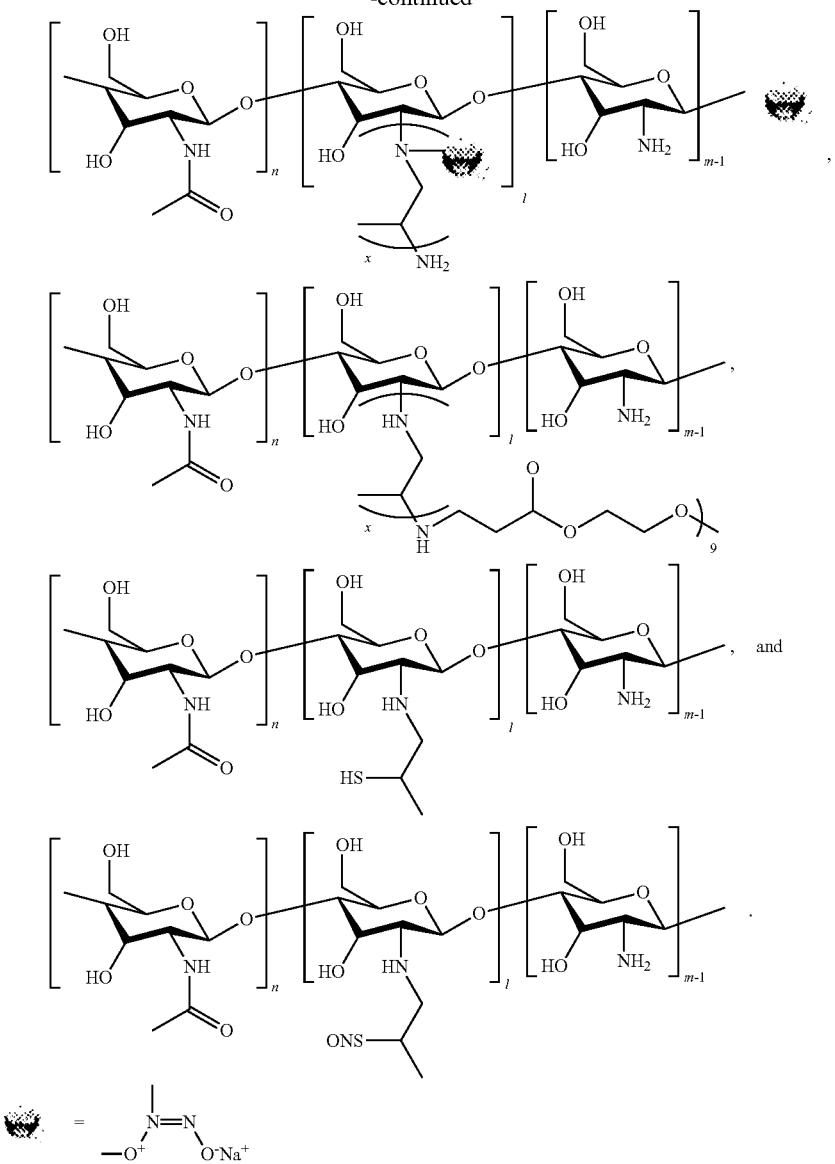

In each of the above structures of formula I and embodiments therein (i.e., Formulae III, VI and VII), when present, m is an integer from 1 to 10,000, preferably 1 to 1000 or 1 to 500; more preferably 1 to 200 or 1 to 100; and most preferably 1 to 50; 1 to 20 or 1 to 10, such as 1, 2, 3, 4, 5, 6, 7, 8, 9 or 10; n is an integer from 1 to 10,000, preferably 1 to 1000 or 1 to 500; more preferably 1 to 200 or 1 to 100; and most preferably 1 to 50; 1 to 20 or 1 to 10, such as 1, 2, 3, 4, 5, 6, 7, 8, 9 or 10; and l is an integer from 1 to 10,000, preferably 1 to 1000 or 1 to 500; more preferably 1 to 200 or 1 to 100; and most preferably 1 to 50; 1 to 20 or 1 to 10, such as 1, 2, 3, 4, 5, 6, 7, 8, 9 or 10.

In an embodiment, the subject matter disclosed herein is directed to a method of delivering nitric oxide to a subject, comprising administering an effective amount of a functionalized polyglucosamine to a subject.

In another embodiment, the subject matter disclosed herein is directed to a method of treating a disease state, comprising administering an effective amount of said polyglucosamine of claim 1 to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases. Preferably, the disease state is cystic fibrosis.

In another embodiment, the subject matter disclosed herein is directed to a method of disrupting, eradicating or preventing a biofilm. This method comprises contacting a surface or area that contains a biofilm or is susceptible to a biofilm forming or occupying some or all of the surface or area with a functionalized polyglucosamine as described herein. The term "biofilm" is intended to mean an aggregate of one or more microorganisms in which cells adhere to each other, usually on a surface. Most any free-floating microorganisms can form a biofilm and/or attach to a surface.

Microorganisms can adhere to a surface or each other through weak, reversible adhesion via van der Waals forces. The microorganisms can more permanently anchor using cell adhesion or structures such as pili.

In yet another embodiment, the subject matter disclosed herein is directed to a pharmaceutical formulation comprising a functionalized polyglucosamine and a pharmaceutically acceptable carrier. Preferably, the functionalized polyglucosamine is water-soluble as described throughout the present disclosure.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 20 ed. 2005). Exemplary pharmaceutically acceptable carriers for the compositions of this invention include, but are not limited to, sterile pyrogen-free water and sterile pyrogen-free physiological saline solution.

The presently disclosed therapeutic compositions, in some embodiments, comprise a composition that includes a presently disclosed nitric oxide-releasing polyglucosamine and a pharmaceutically acceptable carrier. Suitable compositions include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions used in the presently disclosed methods can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

The therapeutic compositions can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds also can be formulated in rectal compositions (e.g., suppositories or retention enemas containing conventional suppository bases, such as cocoa butter or other glycerides), creams or lotions, or transdermal patches.

Pharmaceutical formulations also are provided which are suitable for administration as an aerosol by inhalation. Preferably, the functionalized polyglucosamines described herein are formulated in solution and/or aerosol form. These formulations comprise a solution or suspension of a NO-releasing polyglucosamine described herein. The desired formulation can be placed in a small chamber and nebulized. Nebulization can be accomplished by compressed air or by ultrasonic energy to form a plurality of liquid droplets or solid particles comprising the NO-releasing polyglucosamine. For example, the presently disclosed NO-releasing polyglucosamine can be administered via inhalation to treat bacterial infections related to cystic fibrosis. Cystic fibrosis-related bacterial infections include, but are not limited to stenotrophomonis, *mybacterium avium* intracellulaire and *m. abcessus, burkhoderia cepacia* and *Pseudomonas aeruginosa* (*P. aeruginosa*) infections.

The term "effective amount" is used herein to refer to an amount of the therapeutic composition (e.g., a composition comprising a nitric oxide-releasing polyglucosamine) sufficient to produce a measurable biological response. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including the activity of the composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12. See Freireich et al., *Cancer Chemother Rep.* 50, 219-244 (1966). Drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species. See Freireich et al., *Cancer Chemother Rep.* 50, 219-244 (1966). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

For additional guidance regarding formulation and dose, see U.S. Pat. Nos. 5,326,902; 5,234,933; PCT International Publication No. WO 93/25521; Berkow et al., *The Merck Manual of Medical Information*, Home ed., Merck Research Laboratories: Whitehouse Station, N.J. (1997); Goodman et al., *Goodman & Gilman's the Pharmacological Basis of Therapeutics,* 9th ed. McGraw-Hill Health Professions Division: New York (1996); Ebadi, *CRC Desk Reference of Clinical Pharmacology*, CRC Press, Boca Raton, Fla. (1998); Katzunq, *Basic & Clinical Pharmacology,* 8th ed. Lange Medical Books/McGraw-Hill Medical Pub. Division: New York (2001); Remington et al., *Remington's Pharmaceutical Sciences,* 15th ed. Mack Pub. Co.: Easton, Pa. (1975); and Speight et al., *Avery's Drug Treatment: A Guide to the Properties, Choice, Therapeutic Use and Economic Value of Drugs in Disease Management,* 4th ed. Adis International: Auckland/Philadelphia (1997); Dutch et al., *Toxicol. Leu.,* 100-101, 255-263 (1998).

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180, 082).

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

In some embodiments, one or more additional therapeutic agents can be used in combination with the functionalized polyglucosamine. Such additional agents can be part of a formulation comprising the functionalized polyglucosamine or dosed as a separate formulation prior to, after, or at the same time (concurrently) as a formulation including the functionalized polyglucosamine. Such additional therapeutic agents include, in particular, anti-cancer therapeutics, anti-microbial agents, pain relievers, anti-inflammatories, vasodialators, and immune-suppresants, as well as any other known therapeutic agent that could enhance the alleviation of the disease or condition being treated. "Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The choice of additional therapeutic agents to be used in combination with an NO-releasing polyglucosamine will depend on various factors including, but not limited to, the type of disease, the age, and the general health of the subject, the aggressiveness of disease progression, and the ability of the subject to tolerate the agents that comprise the combination.

A variety of chemical compounds, also described as "antineoplastic" agents or "chemotherapeutic agents" can be used in combination with the presently disclosed NO-releasing polyglucosamines used in the treatment of cancer. Such chemotherapeutic compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapetic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, can be used as part of the presently disclosed cancer treatments. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, a-amanitine and other fungal amatoxins, cordycepin (3'-deoxyadenosine), dichlororibofuranosyl benzimidazole, rifampicine, streptovaricin, and streptolydigin also can be combined with functionalized polyglucosamines to provide a suitable cancer treatment.

Thus, current chemotherapeutic agents that can be used in combination with the presently described NO-releasing functionalized polyglucosamines include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chjlorambucil, bisulfan, nitrosurea, dactinomycin, duanorubicin, doxorubicin, bleomycin, pilcomycin, tamoxifen, taxol, transplatimun, vinblastin, and methotrexate, and the like.

As used herein, the term "antimicrobial agent" refers to any agent that kills, inhibits the growth of, or prevents the growth of a babteria, fungus, yeast, or virus. Suitable antimicrobial agents that can be incorporated into the presently disclosed NO-releasing functionalized polyglucosamines to aid in the treatment or prevention of a microbial infection, include, but are not limited to, antibiotics such as vancomycin, bleomycin, pentostatin, mitoxantrone, mitomycin, dactinomycin, plicamycin and amikacin. Other antimicrobial agents include antibacterial agents such as 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefininox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clindamycin phosphate, clomocycline, colistin, cyclacillin, dapsone, demecicycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin and vancomycin. Antimicrobial agents can also include anti-fungals, such as amphotericin B, azaserine, candicidin(s), chlorphenesin, dermostatin(s), filipin, fungichromin, mepartricin, nystatin, oligomycin(s), perimycin A, tubercidin, imidazoles, triazoles, and griesofulvin.

In some embodiments, the NO-releasing polyglucosamine can be incorporated into polymeric films. Such incorporation can be through physically embedding the polyglucosamine into polymer surfaces, via electrostatic association of the polyglucosamine onto polymeric surfaces, or by covalent attachment of functionalized polyglucosamine onto reactive groups on the surface of a polymer. Alternatively, the functionalized polyglucosamine can be mixed into a solution of liquid polymer precursor, becoming entrapped in the polymer matrix when the polymer is cured. Polymerizable groups can also be used to further functionalize the functionalized polyglucosamine, whereupon, the polyglucosamine can be co-polymerized into a polymer during the polymerization process. Suitable polymers into which the NO-releasing polyglucosamine can be incorporated include polyolefins, such as polystyrene, polypropylene, polyethylene, polytetrafluoroethylene, and polyvinylidene, as well as polyesters, polyethers, polyurethanes, and the like. In particular, polyurethanes can include medically segmented polyurethanes. Medically segmented polyurethanes can also include one or more expander moieties, such as alkylene chains, that add additional length or weight to the polymer. Such polyurethanes are also generally nontoxic. One example of a medically segmented polyurethane is TECOFLEX®.

Polymeric films containing NO-releasing polyglucosamines can be used to coat a variety of articles, particularly surgical tools, biological sensors, and medical implants to prevent platelet adhesion, to prevent bacterial infection, to act as a vasodilator. These articles can be of use in vascular medical devices, urological medical devised, biliary medical devices, gastrointestinal medical devices, medical devices adapted for placement at surgical sites, and medical devices adapted for placement on skin wounds or openings. Thus, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

In some embodiments, the device being coated can have a metallic surface, such as, for example, stainless steel, nickel, titanium, aluminum, copper, gold, silver, platinum, and combinations thereof. In some embodiments, the films or polymers containing the NO-releasing polyglucosamine can be used to coat non-metallic surfaces, such as glass or fiber (e.g., cloth or paper).

Additionally, polymers containing NO-releasing polyglucosamine can be used to form the devices, themselves. For example, the polymers can be fashioned into storage bags for blood or tissue or as wound dressings.

Surfaces that can be contacted with a functionalized polyglucosamine to prevent or disrupt biofilms include those selected from the group consisting of medical devices, plumbing fixtures, condenser coils, optical surfaces, boat hulls and aircrafts. Other non-limiting examples include counter tops, windows, appliances, hard floors, rugs, tubs, showers, mirrors, toilets, bidets, bathroom fixtures, sinks, refrigerators, microwaves, small kitchen appliances, tables, chairs, cabinets, drawers, sofas, love seats, benches, beds, stools, armoires, chests, dressers, display cabinets, clocks, buffets, shades, shutters, entertainment centers, arm rails, lamps, banisters, libraries, cabinets, desks, doors, shelves, couches, carts, pianos, statues and other art, racks, fans, light fixtures, pool tables, ping pong tables, soccer tables, card tables, tools (e.g., hand powered and/or hand held tools, electrical tools, air powered tools, etc.), telephones, radios, televisions, stereo equipment, CD and DVD players, analog and digital sound devices, palm computers, laptop computers, desktop and tower computers, computer monitors, mp3 players, memory storage devices, cameras, camcorders, vehicle surfaces (e.g., windshield; tires; metal, fiberglass, composite material and/or plastic outer surfaces; fabric and/or vinyl outer surfaces; fabric, vinyl, and/or leather interior surfaces; metal, plastic, wood and/or composite material interior surfaces, glass interior surfaces, etc.), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. Any surface where it is desirable to cause one or more types of liquids to run off of a surface, to not be absorbed into a surface, and/or to not stain a surface, can be a substrate. For example, a surface that is exposed to environmental conditions. Also where the surface can become a locus for microbial adhesion such as medical devices that contact bodily tissues or fluids is particularly preferred.

Medical devices such as catheters, which are adapted for movement through blood vessels or other body lumens, are typically provided with low-friction outer surfaces. If the surfaces of the medical devices are not low-friction surfaces, insertion of the devices into and removal of the devices from the body lumens becomes more difficult, and injury or inflammation of bodily tissue may occur. Low friction surfaces are also beneficial for reducing discomfort and injury that may arise as a result of movement between certain long term devices (e.g., long term catheters) and the surrounding tissue, for example, as a result of patient activity. Medical devices include a variety of implantable and insertable medical devices (also referred to herein as "internal medical devices"). Examples of such medical devices include, devices involving the delivery or removal of fluids (e.g., drug containing fluids, pressurized fluids such as inflation fluids, bodily fluids, contrast media, hot or cold media, etc.) as well as devices for insertion into and/or through a wide range of body lumens, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth. Non-limiting, specific examples of internal medical devices include vascular devices such as vascular catheters (e.g., balloon catheters), including balloons and inflation tubing for the same, hydrolyser catheters, guide wires, pullback sheaths, filters (e.g., vena cava filters), left ventricular assist devices, total artificial hearts, injection needles, drug delivery tubing, drainage tubing, gastroenteric and colonoscopic tubing, endoscopic devices, endotracheal devices such as airway tubes, devices for the urinary tract such as urinary catheters and ureteral stents, and devices for the neural region such as catheters and wires, trocar needles, bone anchors, bone screws, protective platings, joint replacements, electrical leads, biosensors, probes, sutures, surgical drapes, wound dressings, and bandages. Many devices in accordance with the invention have one or more portions that are cylindrical in shape, including both solid and hollow cylindrical shapes.

Solid substrate materials can include organic materials (e.g., materials containing 50 wt % or more organic species) such as polymeric materials, and inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others). Specific examples of non-metallic inorganic materials can be materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Further, the NO-releasing polyglucosamine can be incorporated into detergents, such as, but not limited to, anti-microbial soaps. For example, NO-release from functionalized polyglucosamine embedded in bar soaps can be triggered by contact with water and/or a drop in pH upon use. As the outer surface of the bar is eroded or dissolved, additional functionalized polyglucosamine within the bar surface become exposed for subsequent uses of the bar. NO-releasing polyglucosamine also can be suspended in liquid soaps. Such soaps or detergents can be used for personal hygiene or to provide anti-microbial treatments for fibers. Such soaps or detergents can also be used to treat household surfaces or any surface in a hospital or other medical environment that may be exposed to microbes such as bacteria, fungi or viruses.

The term "biocompatible" refers herein to organic solvents that do not induce toxic or unwanted side effects when administered to a patient in certain amounts.

The formulations include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

The functionalized polyglucosamines also include those having quaternization of any basic nitrogen-containing group therein.

The discussion herein is, for simplicity, provided without reference to stereoisomerism. Those skilled in the art will appreciate that the polyglucosamines described herein can contain one or more asymmetric centers and thus occur as racemates and racemic mixtures, single optical isomers, individual diastereomers, and diastereomeric mixtures. All such isomeric forms of these compounds are expressly included in the present invention.

The present invention is explained in greater detail in the following non-limiting Examples.

EXAMPLES

1. Synthesis of NO-Releasing Chitosan Oligosaccharides

Chitosan oligosaccharides were synthesized by the oxidation (hydrogen peroxide) (Kim, S. K.; Rajapakse, N. Enzymatic production and biological activities of chitosan oligosaccharides (COS): A review. *Carbohydr. Polym.* 2005, 62, 357-368) or enzymatic degradation of chitosan polysaccharides. The resulting water soluble chitosan oligosaccharides were modified by a cationic ring opening of aziridine compounds (including but not limited to aziridine and 2-methyl aziridine) to impart secondary amine moieties, followed by the reaction with high pressure NO under basic condition ("charging") to yield water soluble NO-releasing chitosan oligosaccharides.

Materials and Methods

Medium molecular weight chitosan, 2-methyl aziridine (MAz), rhodamine B isothiocyanate (RITC), poly(ethylene glycol) methyl ether acrylate (average Mn=480) (PEG), fetal bovine serum (FBS), Dulbecco's Modified Eagle's Medium (DMEM), phenazine methosulfate (PMS), 3-(4,5-dimethyl-thiazol-2-yl)-5-(3-carboxymethoxyphenyl)-2-(4-sulfophenyl)-2H-tetrazolium inner salt (MTS), trypsin, phosphate buffered saline (PBS), and penicillin streptomycin (PS) were purchased from the Aldrich Chemical Company (Milwaukee, Wis.). *Pseudomonas aeruginosa* (ATCC #19143) was obtained from the American Type Culture Collection (Manassas, Va.). Trypic soy broth (TSB) and Tryptic soy agar (TSA) are purchased from Becton, Dickinson, and Company (Franklin Lakes, N.J.). L929 mouse fibroblasts (ATCC #CCL-1) were obtained from the University of North Carolina Tissue Culture Facility (Chapel Hill, N.C.). Distilled water was purified with a Millipore Milli-Q Gradient A-10 water purification system (Bedford, Mass.). Syto 9 green fluorescent nucleic acid stain was purchased from Life Technologies (Grand Island, N.Y.). Common laboratory salts and solvents were purchased from Fisher Scientific (Pittsburgh, Pa.). All materials were used as received without further purification unless noted otherwise. Nuclear magnetic resonance (NMR) spectra were recorded on a 400 MHz Bruker instrument. Elemental (carbon, hydrogen, and nitrogen or CHN) analysis was performed using a PerkinElmer Elemental Analyzer Series 2400 instrument (Waltham, Mass.).

Chitosan oligosaccharides were prepared by oxidative degradation using hydrogen peroxide. Medium molecular weight chitosan (2.5 g) was suspended in a hydrogen peroxide solution (15 or 30 wt %) under stirring for 1 h at 65-85° C. Following the removal of undissolved chitosan by filtration, chitosan oligosaccharides were precipitated from solution by adding acetone to the filtrate. The precipitate was collected by centrifugation, washed twice with ethanol, and dried under vacuum at room temperature. The viscosity of the chitosan oligosaccharides was measured in a solution of NaCl (0.20 M) and $CH_3COOH$ (0.10 M) at 25° C. using an Ubbleohde capillary viscometer. Oligosaccharide molecular weight was determined using the classic Mark-Houwink equation (i.e., $[\eta]=1.81 \times 10^{-3} M^{0.93}$). Maghami (1988).

Control of the molecular weight (Mw) was achieved by varying the concentration of hydrogen peroxide and degradation temperature. The viscosity of the chitosan oligosaccharides was determined in a solution of sodium chloride (0.20 M) and acetic acid (0.10 M) using an Ubbleohde capillary viscometer. Du, J.; Hsieh, Y. L. Nanofibrous membranes from aqueous electrospinning of carboxymethyl chitosan. *Nanotechnology* 2008, 19, 125707. In combination with the Mark-Houwink equation (i.e., $[i]=1.81\times10^{-3} M^{0.93}$) molecular weights were determined as a function of processing conditions. Collectively, larger concentrations of hydrogen peroxide and elevated degradation temperatures led to lower molecular weight chitosan. As shown in Table 1, chitosan oligosaccharides of ~10 kD molecular weight were prepared in 15 wt % hydrogen peroxide at 65° C. for 1 h. Increasing the degradation temperature to 85° C. resulted in significantly smaller size (MW~5 kD).

TABLE 1

Table 1 Degradation conditions and elemental analysis of chitosan oligosaccharides of different molecular weights.

| Chitosan oligosaccharides | $M_v{}^a$ | T (° C.) | $[H_2O_2]$ (wt %) |
|---|---|---|---|
| 2.5k | 2657 | 85 | 30 |
| 5k | 5370 | 85 | 15 |
| 10k | 10142 | 65 | 15 |

$^a$viscosity average molecular weight as determined by classic Mark-Houwink equation (i.e., $[\eta] = 1.81 \times 10^{-3} M^{0.93}$).

When both a larger concentration of hydrogen peroxide (i.e., 30 wt %) and elevated temperature (i.e., 85° C.) were adopted, the molecular weight of chitosan oligosaccharides decreased further (~2.5 kD) were achieved. As shown in Table 2, the CHN elemental analysis of the oligosaccharides indicated an overall nitrogen content of 6.3 wt %.

TABLE 2

Elemental (CHN) analysis of chitosan oligosaccharides and secondary amine-functionalized derivatives.

| Materials | C (%) | H (%) | N (%) |
|---|---|---|---|
| Chitosan oligosaccharides$^a$ | 42.2 ± 1.6 | 6.8 ± 0.1 | 6.3 ± 0.2 |
| Chitosan 1-5k | 43.5 ± 1.2 | 7.7 ± 0.3 | 8.9 ± 0.1 |
| Chitosan 2-5k | 44.7 ± 1.8 | 5.4 ± 0.2 | 10.8 ± 0.8 |
| Chitosan 3-5k | 51.0 ± 0.2 | 9.0 ± 0.2 | 3.1 ± 0.1 |
| Chitosan 2-2.5k | 43.7 ± 0.7 | 8.5 ± 0.2 | 10.9 ± 0.1 |
| Chitosan 2-10k | 44.7 ± 1.8 | 8.4 ± 0.2 | 10.8 ± 0.8 |

$^a$chitosan oligosaccharides before the grafting of 2-methyl aziridine.
Each parameter was analyzed with multiple replicates (n = 3).

Figure 5A:
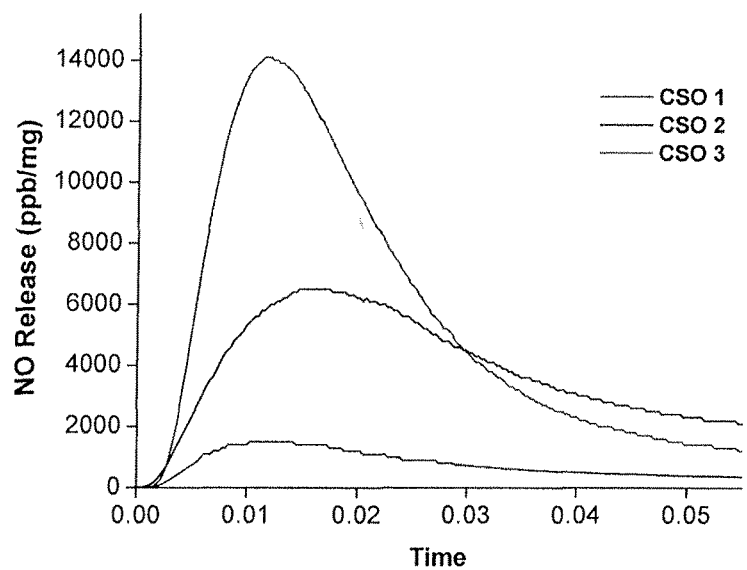
FIGS. 5A & 5B depicts (A) Real time NO release profiles for certain NO-releasing chitosan oligosaccharides; and (B) plot of t[NO] vs time for certain NO-releasing chitosan oligosaccharides.
Figure 5B:
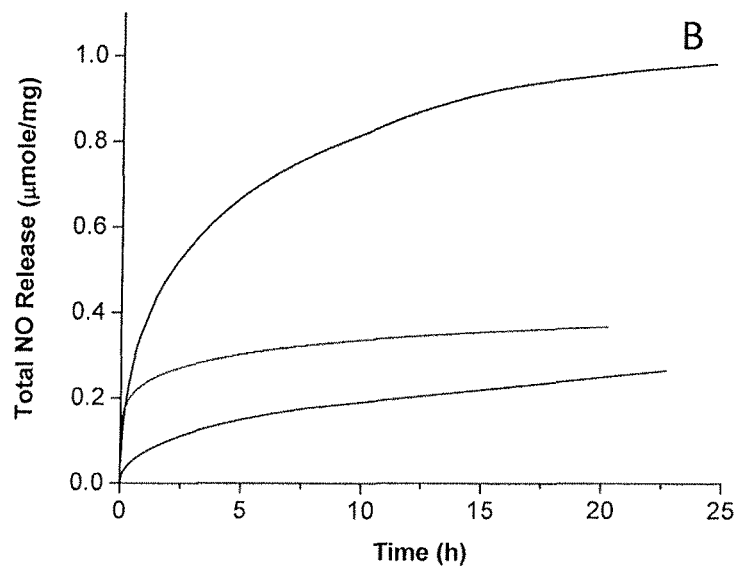

2-methyl aziridine (MAz) was grafted onto the chitosan oligosaccharides at different feed ratios (i.e., 2:1 and 1:1) to alter the secondary amine functionalization and NO storage. Increasing the feed ratio of 2-methyl aziridine to primary amines from 1:1 (CSO 1; Chitosan 1-5k) to 2:1 (CSO 2; Chitosan 2-5k) resulted in greater NO storage (e.g., ~0.30 to 0.87 μmol/mg, respectively). As shown in FIGS. 5A & B, the NO flux and storage of Chitosan 1/NO-5k were lower than Chitosan 2/NO-5k, a result that may be attributable to the smaller amine concentration of Chitosan 1-5k (~8.9 wt %) compared to Chitosan 2-5k (~10.8 wt %).

Schemes A and B depict routes for preparing NO-releasing chitosan oligosaccharides described herein.
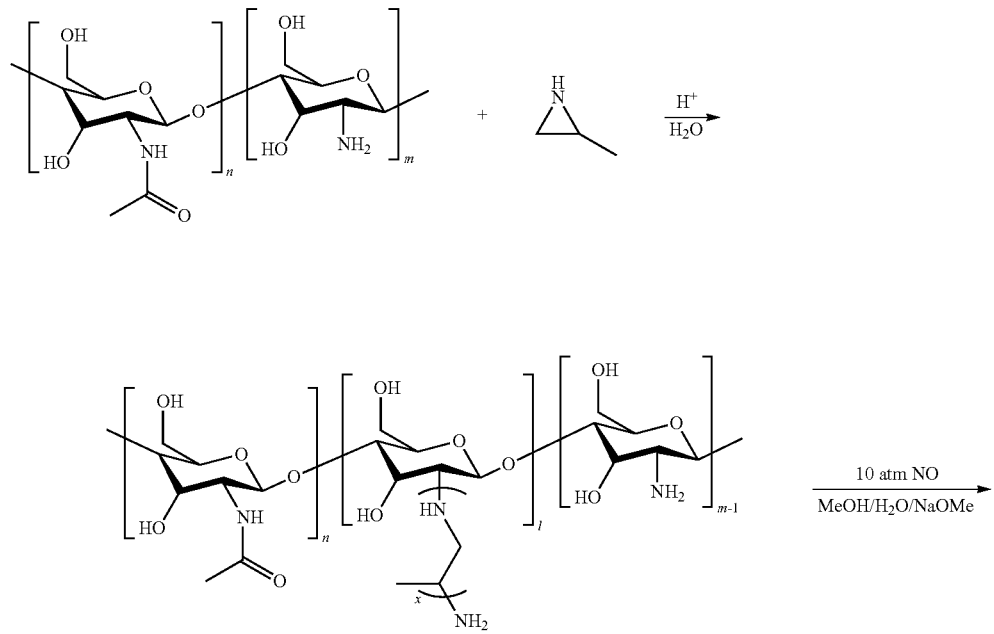
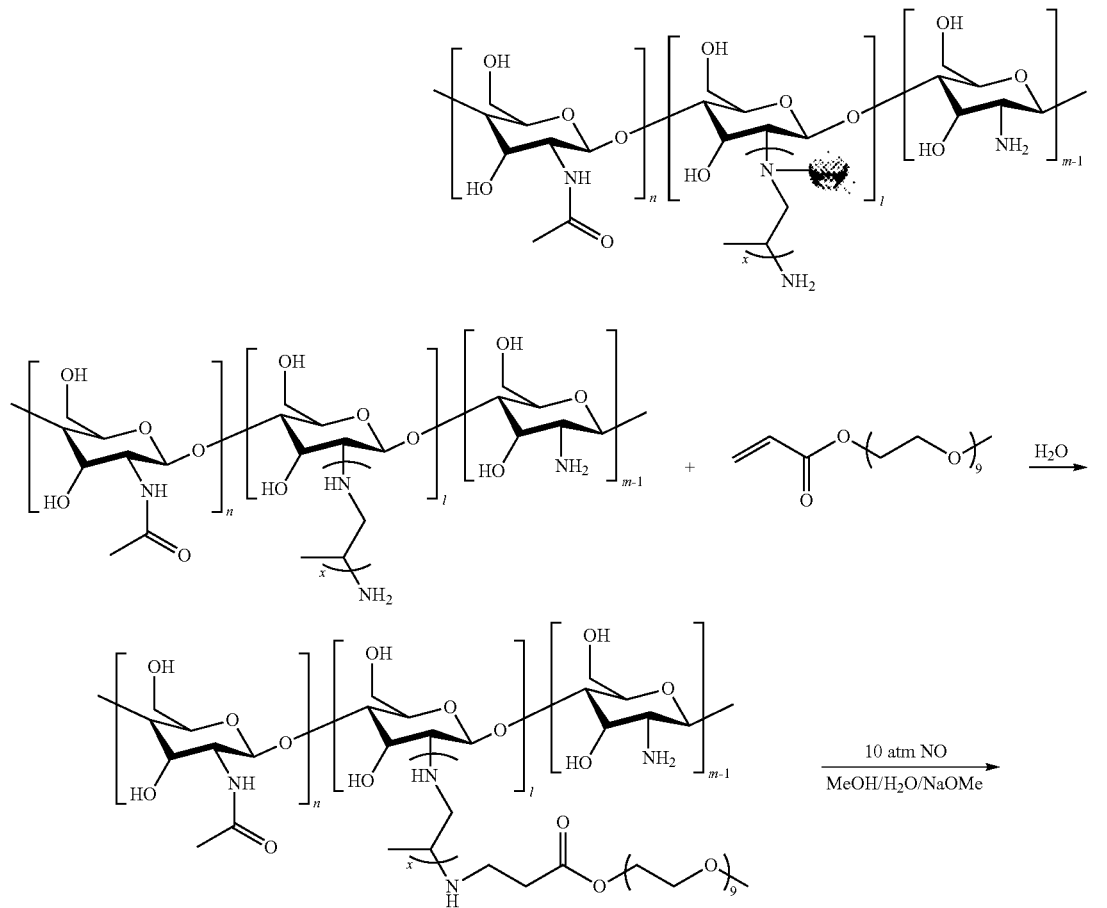

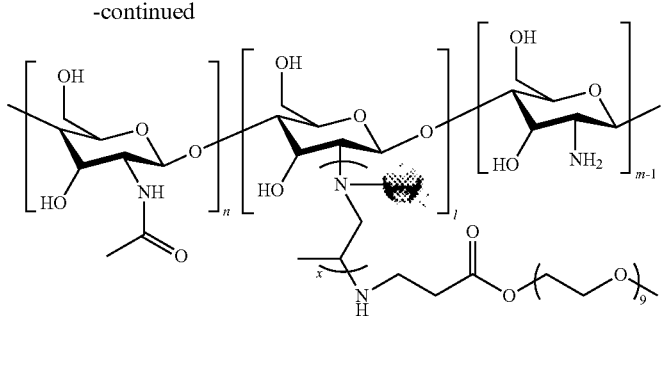

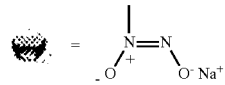

In Scheme A, CSO 1 (x=1); CSO 2 (x=2); CSO 1-NO (x=1); CSO 2-NO (x=2). In scheme B, CSO 3 (x=2); CSO 3-NO (x=2). Scheme A above is a synthetic route for preparing secondary amine- and diazeniumdiolate-functionalized chitosan oligosaccharides derivatives involves grafting of 2-methyl aziridine onto primary amines of chitosan oligosaccharides (CSO 1, 2) and diazeniumdiolation of the resulting materials (CSO 1, 2-NO). Scheme B above is a synthetic route for preparing secondary amine- and diazeniumdiolate-functionalized chitosan oligosaccharides derivatives involves PEGylation of 2-methyl aziridine-grafted-chitosan oligosaccharide (CSO 3) and the diazeniumdiolation of the resulting material (CSO 3-NO).

Schemes A' and B' depict a synthesis route for chitosan oligosaccharides disclosed herein:

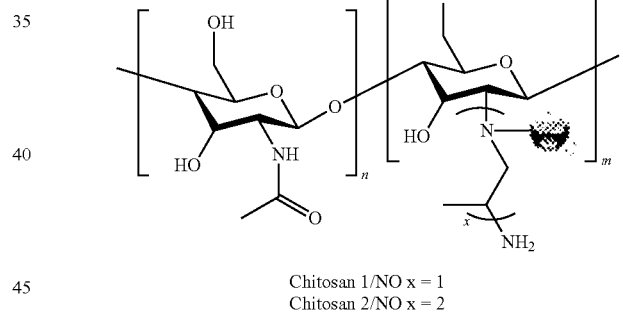

Chitosan 1 x = 1
Chitosan 2 x = 2

Scheme A'

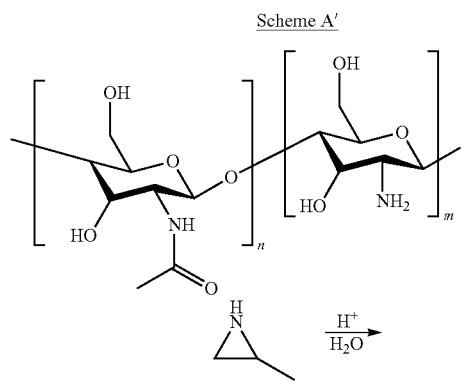

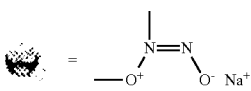

Chitosan 1/NO x = 1
Chitosan 2/NO x = 2

Scheme B'

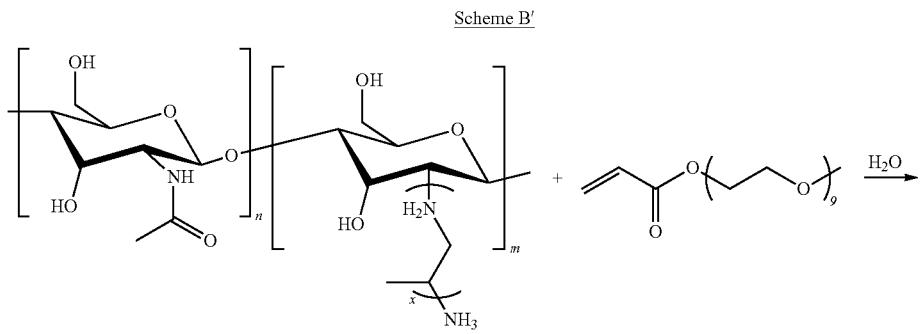

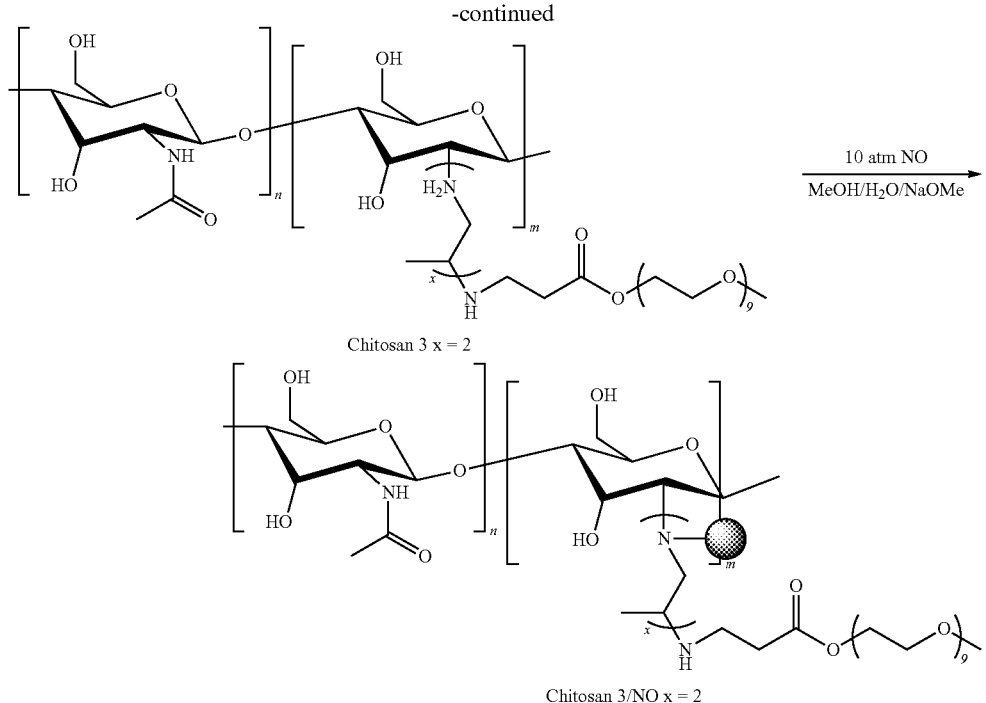

Chitosan 3 x = 2

Chitosan 3/NO x = 2

Reaction of the secondary amine-functionalized chitosan oligosaccharides (Chitosan 1, Chitosan 2, and Chitosan 3) with NO (10 atm under basic conditions) yielded N-diazeniumdiolate NO donor-functionalized chitosan oligosaccharides (Chitosan 1/NO, Chitosan 2/NO, and Chitosan 3/NO). The NO conjugation ("charging") solvent affects the charging efficiency and potentially total NO storage. Carpenter, A. W.; Slomberg, D. L.; Rao, K. S.; Schoenfisch, M. H., Influence of scaffold size on bactericidal activity of nitric oxide-releasing silica nanoparticles. *ACS Nano* 2012, 5, 7235-7244. Aqueous solutions were necessary in order to adequately dissolve the chitosan oligosaccharides. To examine the influence of water concentration on N-diazeniumdiolate conversion efficiency, mixtures of methanol (a common charging solvent) (Carpenter (2012); Stasko, N. A.; Schoenfisch, M. H. Dendrimers as a scaffold for nitric oxide release. *J. Am. Chem. Soc.* 2006, 128, 8265-8271) and water were prepared (10:0, 9:1, 8:2, 7:3, and 6:4 v/v) and the pH was adjusted to above 10 by adding sodium methoxide.

Scheme C depicts a route for preparing nitrosothiol NO-releasing chitosan oligosaccharides as described herein.

Scheme C

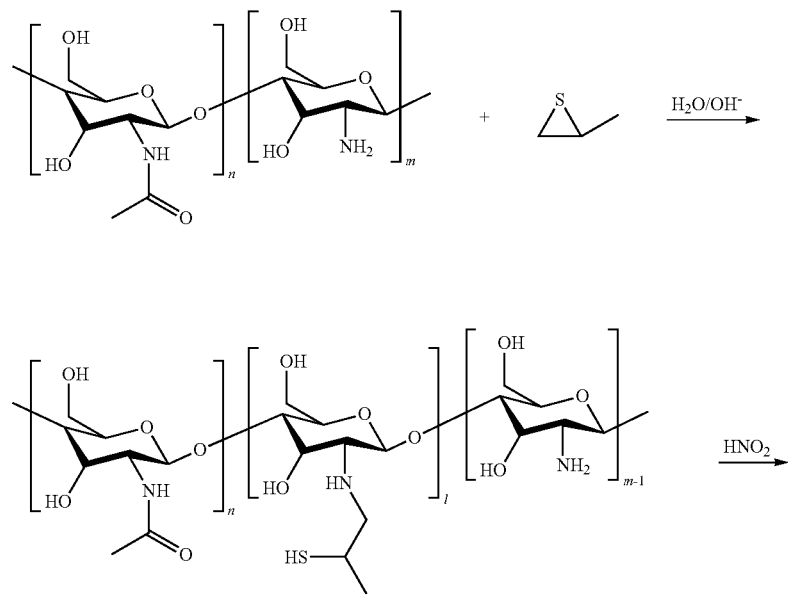

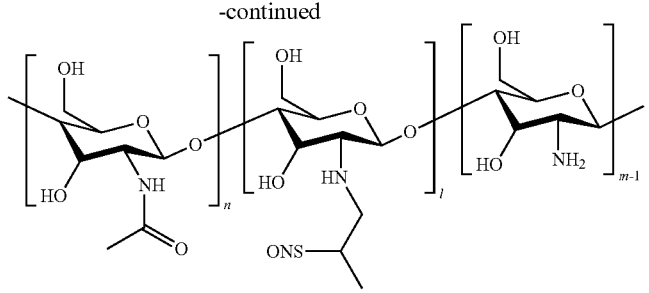

Scheme D depicts diazeniumdiolate conjugation and release of 2 NO from a conjugated diazeniumdiolate.

Scheme D

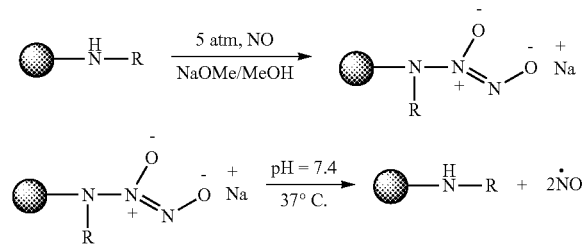

Secondary Amine-Functionalized Chitosan Oligosaccharides:

2-methyl aziridine (MAz) grafted chitosan oligosaccharides were synthesized following a previously reported procedure. Wong, K.; Sun, G. B.; Zhang, X. Q.; Dai, H.; Liu, Y.; He, C. B.; Leong, K. W. PEI-g-chitosan, a novel gene delivery system with transfection efficiency comparable to polyethylenimine in vitro and after liver administration in vivo. *Bioconj. Chem.* 2006, 17, 152-158. Briefly, a mixture of concentrated HCl (11 µL), water (100 µL) and MAz with a 1:1 (CSO 1; Chitosan 1) or 2:1 (CSO 2; Chitosan 2) molar ratio to primary amines on the chitosan oligosaccharides was added dropwise to a solution of chitosan oligosaccharides (100 mg) in deionized water (5 mL). The resulting solution was stirred at room temperature for 5 d, and then at 75° C. for 24 h. The product was purified by dialysis and collected by lyophilization. Any high molecular weight poly(2-methyl aziridine) in the product was removed by washing with methanol, and the resulting material was dried under vacuum at room temperature. Chitosan 2 was then dissolved in water at pH 10.0. The primary amine on the chitosan oligosaccharides was functionalized by adding poly(ethylene glycol) methyl ether acrylate to generate Chitosan 3. The resulting PEG-functionalized chitosan oligosaccharide derivative was purified by dialysis and collected by lyophilization. $^1$H NMR data of Chitosan 1 and Chitosan 2 (400 MHz, CD$_3$OD, δ): 0.8-1.1 (NH$_2$CH(CH$_3$)CH$_2$NH), 1.9 (C7: CHNHCOCH$_3$), 2.3-2.7 (NH$_2$CH(CH$_3$)CH$_2$NHCH, C2: NH$_2$CH(CH$_3$)CH$_2$NHCH), 3.3-4.0 (C3, C4, C5, C6: OHCH, OCHCH(OH)CH(NH$_2$)CH, OHCH$_2$CH, OHCH$_2$CH), 4.4 (C1: OCH(CHNH$_2$)O). $^1$H NMR data of Chitosan 3 (400 MHz, CD$_3$OD, δ): 0.8-1.1 (NH$_2$CH(CH$_3$) CH$_2$NH), 1.9 (C7: CHNHCOCH$_3$), 2.3-2.7 (NH$_2$CH(CH$_3$) CH$_2$NHCH, C2: NH$_2$CH(CH$_3$)CH$_2$NHCH), 3.2 (OCH$_2$CH$_2$OCH$_3$), 3.3-4.0 (OCH$_2$CH$_2$O and C3, C4, C5, C6: OHCH, OCHCH(OH)CH(NH$_2$)CH, OHCH$_2$CH, OHCH$_2$CH), 4.4 (C1: OCH(CHNH$_2$)O).

N-Diazeniumdiolate-Functionalized Chitosan Oligosaccharides:

Secondary amine-functionalized chitosan oligosaccharides (CSO 1, Chitosan 1, CSO 2, Chitosan 2, chitosan 3 and CSO 3) and 5.4 mM sodium methoxide (75 µL) were added to a methanol/water mixture (2 mL) of different v/v ratios (e.g., 10:0, 9:1, 8:2, 7:3, 6:4). The suspension was added to vials in a Parr hydrogenation vessel, which was purged rapidly (5-10 s) with argon three times followed by three longer argon purge cycles (10 min) to remove residual oxygen from the solution. The Parr hydrogenation vessel was then pressurized to 10 atm with NO gas purified over KOH pellets (to remove NO degradation products) and maintained at 10 atm for 3 d. The same argon purging protocol was performed to remove unreacted NO and degradation products from the solution prior to removing the vials from the vessel.

Fluorescently-Labeled Chitosan Oligosaccharides:

These chitosan oligosaccharides were prepared following a previously reported procedure. Tokura, S.; Ueno, K.; Miyazaki, S.; Nishi, N., Molecular weight dependent antimicrobial activity by chitosan. *Macromol. Symp.* 1997, 120, 1-9. Briefly, chitosan oligosaccharides (50 mg) were dissolved in water (2 mL) at pH 9.0. Rhodamine B isothiocyanate (RITC) was added to the solution in a 1:100 molar ratio to the primary amine of the chitosan oligosaccharides prior to the grafting of 2-methyl aziridine. The solution was stirred at room temperature for 3 d in the dark. Subsequent dialysis and lyophilization yielded the RITC-labeled chitosan oligosaccharides.

By tuning the ratio of MAz and primary amine (e.g., 1:1 CSO 1 and Chitosan 1, 2:1 CSO 2 and Chitosan 2), the number of MAz repeating units grafted onto the chitosan oligosaccharides was tunable (supporting NMR data), leading to a range of secondary amine concentrations and NO storage. Acrylate-functionalized PEG chains were conjugated to the primary amines on CSO 2 and Chitosan 2 by the Michael addition reaction to yield PEG-modified scaffolds (e.g., CSO 3 and Chitosan 3, See, schemes B and B'). Grafting of 2-methyl aziridine to the oligosaccharides increased the corresponding nitrogen content from 6.3 to 8.9 and 10.8 wt % for CSO 1 and Chitosan 1 and for CSO 2 and Chitosan 2, respectively. The PEGylation of CSO 2 and Chitosan 2 led to a corresponding decrease in nitrogen content (3.1 wt %) (CSO 3 and Chitosan 3).

Figure 4A:
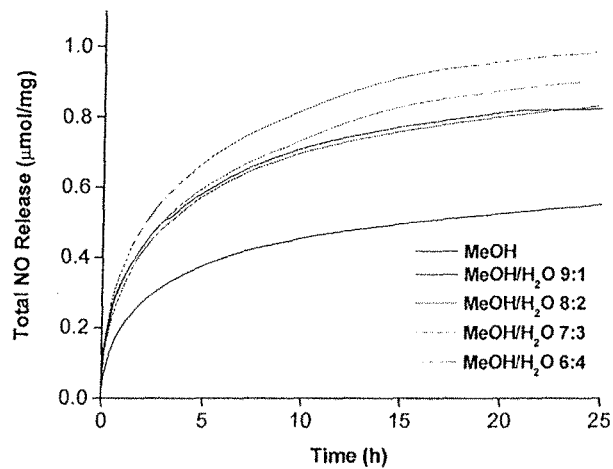
FIG. 4A depicts the release profile of certain chitosan oligosaccharides CSO 2-NO in different NO conjugation solvents. Methanol:$H_2O$ 7:3 resulted in total NO storage of 0.87 μmol/mg.
Figure 4B:
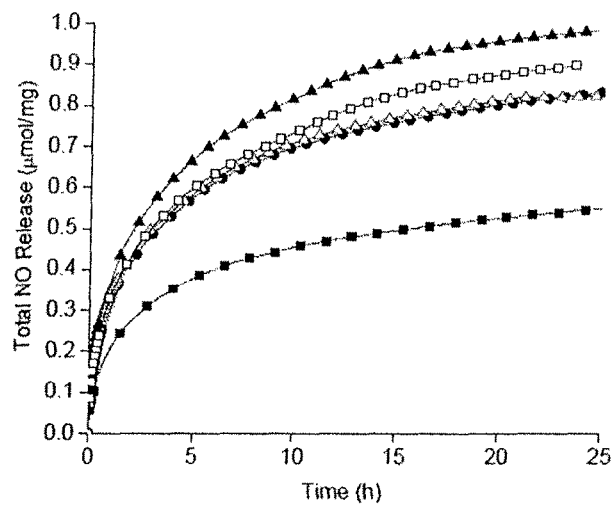
FIG. 4B depicts specific data points for the nitric oxide release profiles of Chitosan 2/NO-5k in methanol (solid square), methanol/water 9:1 (solid circle), 8:2 (open triangle), 7:3 (solid triangle), and 6:4 v/v (open square).

2. Nitric Oxide Charging, Storage and Release in Functionalized Polyglucosamines The subject matter disclosed herein describes the optimization of charging condition for secondary-amine-functionalized chitosan oligosaccharides (e.g., CSO 1, 2, 3). Mixtures of methanol and water were used as the charging solvents. FIG. 4 shows the NO release profiles for CSO 2-NO charged in different solvents. When the 7:3 methanol/water was used, the maximum total NO storage (e.g., ~0.87 µmol/mg) was yielded.

TABLE 3

Nitric oxide release characteristics in for secondary amine-functionalized chitosan oligosaccharides (CSO 2; Chitosan 2/NO-5k) PBS (pH = 7.4) at 37° C.

| | MeOH/H$_2$O | | | | |
|---|---|---|---|---|---|
| | 10:0 | 9:1 | 8:2 | 7:3 | 6:4 |
| t[NO] (μmol/mg) | 0.58 ± 0.09 | 0.74 ± 0.12 | 0.81 ± 0.14 | 0.87 ± 0.16 | 0.75 ± 0.18 |
| [NO]$_{max}$ (ppb/mg) | 2648 ± 120 | 4150 ± 70 | 4350 ± 484 | 5500 ± 414 | 5000 ± 572 |
| Half-life (h) | 2.40 ± 0.13 | 2.25 ± 0.02 | 2.05 ± 0.07 | 2.20 ± 0.14 | 2.05 ± 0.25 |

The subject matter disclosed herein describes the control of total NO storage by tuning the ratio of aziridine compounds to the primary amines on the chitosan oligosaccharides. By increasing the use of aziridine compounds, greater secondary amine content and thus total NO storage can be achieved. For example, as shown in FIGS. 5A and B and Tables 4A and B, the synthesis with 2-methyl aziridine/primary amines 2:1 ratio yielded total storage around 0.87 μmol/mg while the ratio 1:1 led to the NO storage of 0.30 μmol/mg. Accordingly, further increase of aziridine compound usage would likely result in more enhanced NO storage. The maximum NO storage (using the 7:3 methanol/water charging solvent ratio) was 0.87 μmol/mg, roughly 4× larger than that for previously reported chitosan polysaccharides (~0.2 μmol/mg). Du, J.; Hsieh, Y. L. Nanofibrous membranes from aqueous electrospinning of carboxymethyl chitosan. *Nanotechnology* 2008, 19, 125707; Kim, S. K.; Rajapakse, N. Enzymatic production and biological activities of chitosan oligosaccharides (COS): A review. *Carbohydr. Polym.* 2005, 62, 357-368; Maghami (1988).

The subject matter disclosed herein describes the control of NO-release kinetics by functionalizing the amine moieties of the secondary amine-functionalized chitosan oligosaccharides (CSO 1, 2). As shown in FIGS. 5A and B and Tables 4A and 4B, chitosan oligosaccharides modified with hydrophilic PEG (CSO 3-NO) exhibited a greater initial NO flux and shorter half-life compared to the counterparts before PEG functionalization (CSO 2-NO).

TABLE 4A

Nitric oxide-release properties of N-diazeniumdiolate NO donor-functionalized chitosan oligosaccharides.

| | t[NO] (μmol/mg) | [NO]$_{max}$ (ppb/mg) | t$_{1/2}$ (h) |
|---|---|---|---|
| CSO 1-NO | 0.30 ± 0.04 | 1600 ± 215 | 3.60 ± 0.13 |
| CSO 2-NO | 0.87 ± 0.16 | 5500 ± 414 | 2.20 ± 0.14 |
| CSO 3-NO | 0.35 ± 0.02 | 12600 ± 2121 | 0.15 ± 0.01 |

Accordingly, the oligosaccharide units will be present in mole ratios that are reflected in the NO release properties. In embodiments, m is from about 0.4 to about 0.9, for example about 0.4, 0.5, 0.6, 0.7, 0.8 or 0.9; n is from about 0.1 to about 0.6, for example about 0.1, 0.2, 0.3, 0.4, 0.5, or 0.6; wherein m and n represent the mole fraction of each unit and the sum of m and n is 1.

TABLE 4B

Nitric oxide-release properties of different N-diazeniumdiolate NO donor-functionalized chitosan oligosaccharides in PBS (pH = 7.4, 37° C.) as measured using a chemiluminescence NO analyzer.

| Material | t[NO]$^a$ (μmol/mg) | t[NO]$^b$ (μmol/mg) | [NO]$_{max}$ (ppb/mg) | t$_{1/2}$ (h) |
|---|---|---|---|---|
| Chitosan 1/NO-5k | 0.30 ± 0.04 | 0.16 ± 0.03 | 1600 ± 215 | 3.60 ± 0.13 |
| Chitosan 2/NO-5k | 0.87 ± 0.16 | 0.52 ± 0.15 | 5500 ± 414 | 2.20 ± 0.14 |
| Chitosan 3/NO-5k | 0.35 ± 0.02 | 0.29 ± 0.01 | 12600 ± 2121 | 0.15 ± 0.01 |
| Chitosan 2/NO-2.5k | 0.84 ± 0.04 | 0.49 ± 0.02 | 7500 ± 550 | 2.06 ± 0.10 |
| Chitosan 2/NO-10k | 0.81 ± 0.05 | 0.47 ± 0 03 | 7350 ± 672 | 2.04 ± 0.05 |

$^a$total NO released and
$^b$NO released over 24 and 4 h (μmol) per milligram of secondary amine-functionalized PPI Each parameter was analyzed with multiple replicates (n = 3).

N-diazeniumdiolate-functionalized chitosan oligosaccharides (1 mg) (CSO 1-NO, Chitosan 1/NO, CSO 2-NO, Chitosan 2/NO, CSO 3-NO, Chitosan 3/NO) in the water/methanol mixture were added into a sample vessel containing 30 mL deoxygenated phosphate buffered saline (PBS) (10 mM, pH=7.4) at 37° C., which initiated NO release. To quantify the NO released, the solution was purged with nitrogen at a flow rate of 70 mL/min to carry the liberated NO to the analyzer. Additional nitrogen flow was supplied to the vessel to match the collection rate of the instrument (200 mL/min). The analysis of NO was terminated when the NO release levels fell to below 10 ppb NO/mg chitosan oligosaccharides. Chemiluminescence data for the NO-releasing chitosan oligosaccharides were represented as: 1) total amount of NO release (t[NO], μmol NO/mg of secondary amine-functionalized chitosan oligosaccharides); 2) the maximum flux of NO release ([NO]max, ppb/mg of secondary amine-functionalized chitosan oligosaccharides); and 3) the half-life of NO release (t$_{1/2}$).

3. Mouse Fibroblast Viability Assay

L929 mouse fibroblasts were grown in DMEM supplemented with 10% (v/v) fetal bovine serum (FBS) and 1 wt % penicillin/streptomycin, and incubated in 5% (v/v) CO$_2$ under humidified conditions at 37° C. After reaching 80% confluency, the cells were trypsinized, seeded onto tissue-culture treated polystyrene 96-well plates at a density of 3×10$^4$ cells/mL and incubated at 37° C. for 48 h. The supernatant was then aspirated prior to adding 200 μL fresh DMEM and 50 μL of a NO-releasing chitosan oligosaccharides solution in PBS to each well. After incubation at 37° C. for 24 h, the supernatant was aspirated and 120 μL mixture of DMEM/MTS/PMS (105/20/1, v/v/v) was added to each well. The absorbance of the resulting colored solution after 1.5 h incubation at 37° C. was quantified at 490 nm using a Thermoscientific Multiskan EX plate reader. The mixture of DMEM/MTS/PMS and untreated cells were used as blank and control, respectively. The cell viability was calculated by equation 1.

$$\text{Cell Viability} = \frac{(Absorbance_{treated\ cell} - Absorbance_{blank})}{(Absorbance_{untreated\ cell} - Absorbance_{blank})} \quad \text{Eq. 1}$$

Figure 8A:
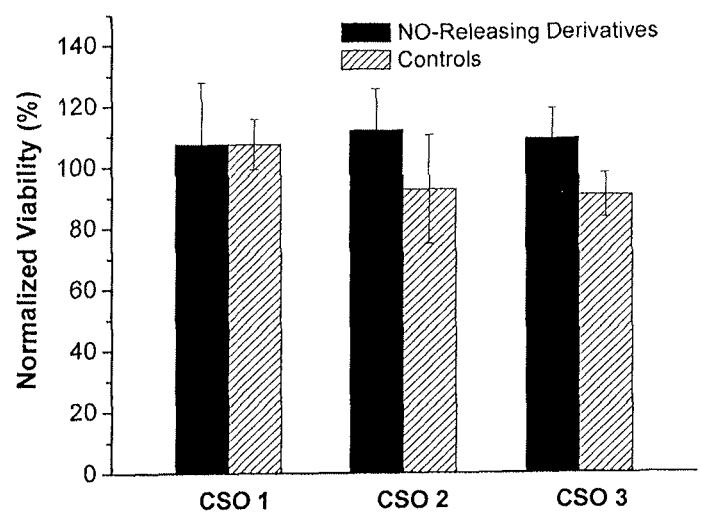
FIGS. 8 A and B depict cytotoxicity in L929 mouse fibroblast. The viability of L929 mouse fibroblasts exposed to control and NO-releasing chitosan oligosaccharides at concentration for 5-log bacteria viability reduction (MBC) against *P. aeruginosa* biofilms. Each parameter was analyzed with multiple replicates (n=3).
Figure 8B:
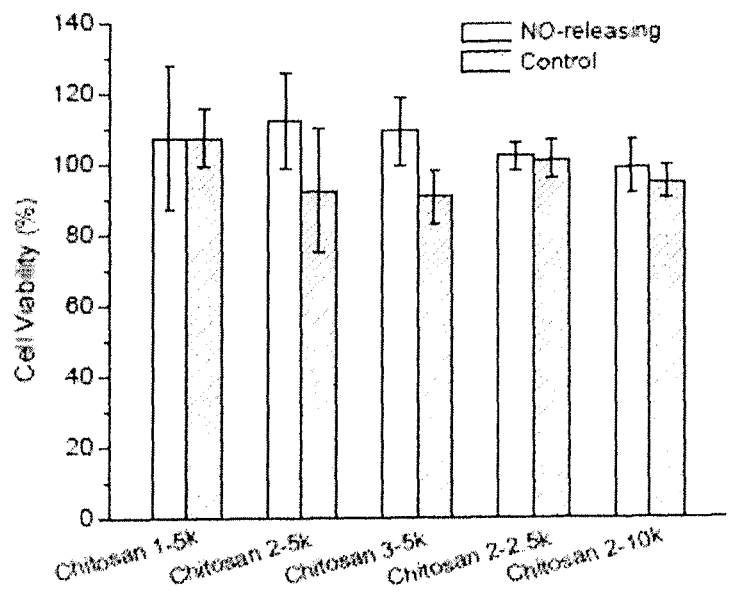
Figures 9A, 9B, 9C, 9D, 9E, 9F:
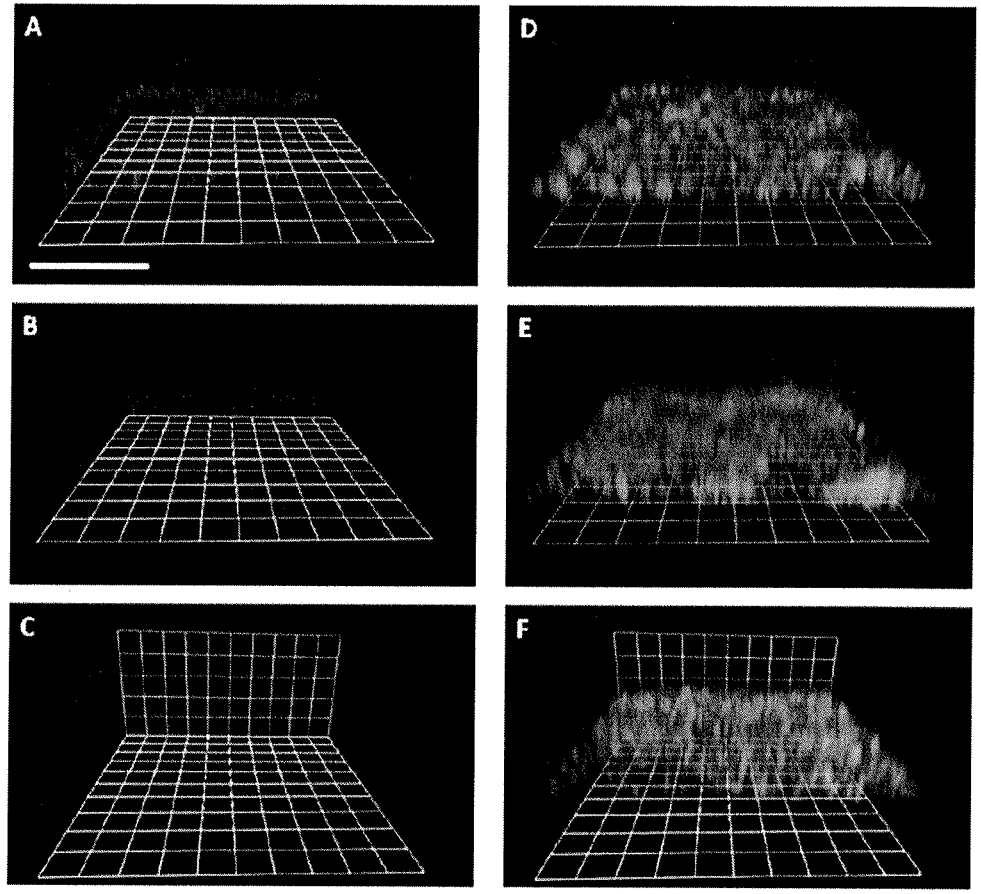
FIG. 9A-F depict confocal fluorescence images of RITC-labeled chitosan oligosaccharide association with *P. aeruginosa* in biofilms (A. Chitosan 2/NO-5k, B. Chitosan 3/NO-5k, C. Chitosan 2-10k) and images of syto 9 labeled biofilms incubated with D) Chitosan 2/NO-5k, E) Chitosan 3/NO-5k and F) Chitosan 2/NO-10k. Green fluorescence of syto 9 indicates the *P. aeruginosa* bacteria embedded in the biofilms. Red fluorescence of RITC indicates the association of RITC-labeled chitosan oligosaccharides with *P. aeruginosa* in biofilms. Scale bar: 40 μm.

4. The cytotoxicity of control and NO-releasing chitosan oligosaccharides were compared by exposing mouse fibroblast cells to the oligosaccharides at the MBCs against *P. aerugionsa* biofilms noted above. The results of the normalized cell viabilities of control and NO-releasing chitosan oligosaccharides after 24 h incubation are shown in FIGS. 8A and B. Regardless of size (i.e., molecular weight), the control and NO-releasing chitosan oligosaccharides were non-toxic against mouse fibroblast cells at the MBCs for the NO-releasing scaffolds, indicating an advantage of these materials as anti-biofilm agents compared to other antibacterial agents. The NO-releasing chitosan oligosaccharides exhibited lower cytotoxicity than the chitosan controls.

5. Bactericidal Assays Under Static Conditions

*P. aeruginosa* bacterial cultures were grown from a frozen (−80° C.) stock overnight in TSB at 37° C. A 500 µL aliquot of the resulting suspension was added into 50 mL fresh TSB and incubated at 37° C. for ~2 h until the concentration reached ~1×10$^8$ colony forming units (CFU)/mL, as confirmed by the OD600, replicate plating and enumeration on nutrient agar. A working bacterial stock was generated by plating the bacterial suspension on TSA and incubating at 37° C. overnight. The TSA bacterial stocks were prepared weekly and stored at 4° C. For bactericidal assays, colonies of *P. aeruginosa* were taken from the TSA plate, dispersed in 3 mL TSB, and incubated at 37° C. overnight. A 500 µL aliquot of culture was added to 50 mL fresh TSB and incubated to a concentration of ~1×10 CFU/mL. The bacteria was collected by centrifugation, resuspended in PBS, and diluted to 1×10$^6$ CFU/mL. The bactericidal efficacy of NO-releasing chitosan oligosaccharides against *P. aeruginosa* was evaluated by incubating the bacteria suspension with NO-releasing chitosan oligosaccharides at 37° C. At 4 h, 100 µL aliquots of the bacterial suspensions were removed, diluted 10-fold in PBS, plated on TSA, and incubated overnight at 37° C. The minimum concentration of NO-releasing chitosan oligosaccharides that resulted in a 3-log reduction of bacterial viability was defined as the minimum bactericidal concentration (MBC) for planktonic studies.

Bacterial viability assays were performed under static conditions to determine the concentration of chitosan required to reduce bacteria viability by 3 logs (i.e., 99.9% killing), which hereafter will be referred to as the minimum bactericidal concentration or MBC. The amount of NO delivered from NO-releasing chitosan oligosaccharides (Table 4) over the time of the assay (4 h) was also examined to quantitatively assess the NO dose necessary for 99.9% bacterial killing. Both MBCs and the bactericidal NO doses required for the chitosan oligosaccharides are provided in Table 5.

TABLE 5

Minimum bactericidal concentration (MBC) and NO doses of NO-releasing chitosan oligosaccharides for 3-log reduction in planktonic *P. aeruginosa* viability.

| Chitosans | MBC (µg/mL) | NO dose (µmol/mL) |
|---|---|---|
| Chitosan 1/NO-5k | 2000 | 0.32 |
| Chitosan 2/NO-5k | 200 | 0.10 |
| Chitosan 3/NO-5k | 1500 | 0.45 |
| Chitosan 2/NO-2.5k | 250 | 0.12 |

Regardless of size (i.e., molecular weight of about 2.5, 5, or 10 kDa), each of the NO-releasing chitosan oligosaccharides (Chitosan 2/NO-2.5 k, Chitosan 2/NO-5 k, Chitosan 2/NO-10 k) exhibited similar bactericidal NO concentrations (i.e., ~10 µmol NO/mL) for 3-log killing (Table 5). Each of the NO-releasing chitosan oligosaccharides studied (including CSO 2-NO-5k) resulted in ≥99.9% killing of *P. aeruginosa*. At equivalent concentrations, the control (non-NO-releasing) chitosan did not lead to a significant reduction in bacterial viability, indicating NO as the bactericidal agent (data not shown).

6. Treatment of *P. aeruginosa* Biofilms with NO-releasing Chitosan Oligosaccharides A CDC bioreactor (Biosurface Technologies, Bozeman, Mont.) was used to grow *P. aeruginosa* biofilms over a 48 h period. Briefly, medical grade silicone rubber substrates were mounted in coupon holders prior to assembling the reactor. The assembled reactor was then autoclaved. The reactor effluent line was clamped, and 1% (v/v) sterile TSB (500 mL) was added aseptically. *P. aeruginosa* was then cultured in TSB to 108 CFU/mL. The reactor was inoculated with an aliquot (1 mL) of this bacterial suspension at a final concentration ~2×105 CFU/mL. The reactor was incubated at 37° C. for 24 h with slow stirring (150 rpm). Following this "batch phase" growth, the reactor media was refreshed continuously with 0.33% (v/v) TSB at 6 mL/min for another 24 h through the effluent line.

*P. aeruginosa* biofilms grown on silicone rubber substrates were exposed to chitosan oligosaccharide in PBS with slight agitation (37° C., 24 h) to determine the minimum bactericidal concentration (MBC) necessary to elicit a 5-log reduction in viability. At 24 h, samples were then sonicated and vortexed to disrupt the biofilm. Aliquots (100 µL) of the bacteria/chitosan suspensions were diluted and plated on TSA. After incubating the TSA plates overnight at 37° C., bacteria viability was determined by counting observed colonies. Of note, the limit of detection for this selected plate counting method is 2.5×103 CFU/mL. As such, biofilm growth conditions were selected to accurately represent a 5-log reduction in viability for biofilms.

Figure 7:
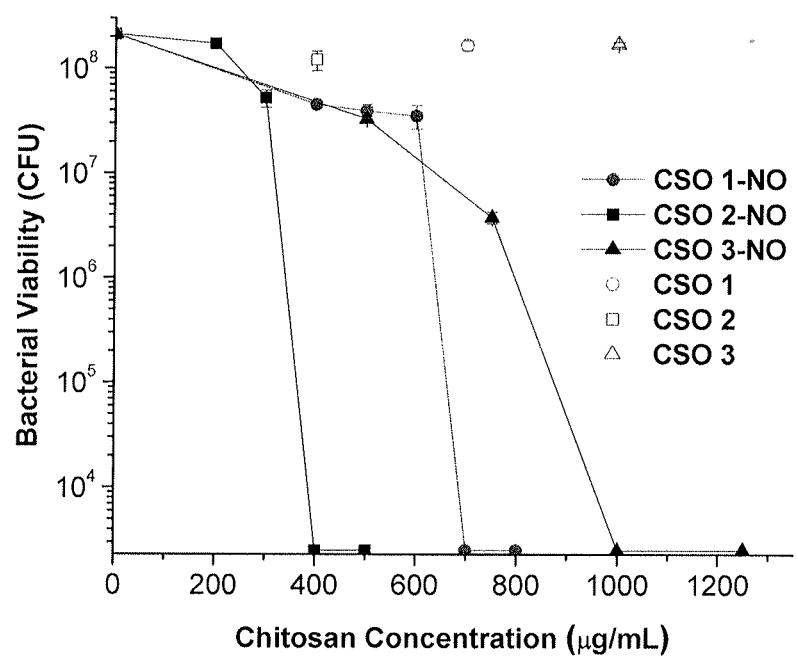
FIG. 7 depicts the data showing NO-releasing CSO led to 5-log reduction of *P. aeruginosa* bacteria with biofilms. Anti-biofilm efficacy of NO-releasing (solid symbols) and control (open symbols) chitosan oligosaccharides (Chitosan 1-5k; CSO 1-NO (sphere), Chitosan 2-5k; CSO 2-NO (square), and Chitosan 3-5k; CSO 3-NO (triangle)) against established *P. aeruginosa* biofilms. Control chitosan oligosaccharides resulted in no significant reduction in bacteria viability.

To evaluate the anti-biofilm activity of NO-releasing chitosan oligosaccharides (e.g., Chitosan 1/NO-5k, Chitosan 2/NO-5k, Chitosan 3/NO-5k), *P. aeruginosa* biofilms were exposed to 0.2-1.3 mg/mL NO-releasing chitosan oligosaccharides for 24 h (corresponding to ~0.17-0.46 µmol NO/mL). After treatment, the biofilms were removed from the silicone rubber substrates by vortexing and sonication to enable viability quantification. Salmon, D. J.; Torres de Holding, C. L.; Thomas, L.; Peterson, K. V.; Goodman, G. P.; Saavedra, J. E.; Srinivasan, A.; Davies, K. M.; Keefer, L. K.; Miranda, K. M. HNO and NO release from a primary amine-based diazeniumdiolate as a function of pH. *Inorg. Chem.* 50, 3262-70. Control experiments were performed to confirm the growth of *P. aeruginosa* biofilms using the selected protocol. As shown in FIG. 7, the viability of *P.*

*aeruginosa* in the biofilm was ~2×10⁸ CFU when exposed only to PBS. The chitosan concentrations for 5-log reduction of biofilm bacteria viability (MBC) were 400, 700, and 1000 μg/mL for Chitosan 2/NO-5k, Chitosan 1/NO-5k, and Chitosan 3/NO-5k, respectively. Chitosan 2/NO-5k exhibited the greatest anti-biofilm efficacy, a likely result due to both increased NO storage/release and rapid association with the negatively charged bacteria. Although Chitosan 1/NO-5k and Chitosan 3/NO-5k stored similar levels of NO (~0.3 μmol/mg), Chitosan 1/NO-5k was more effective at eradicating the biofilm bacteria (MBC 700 μg/mL) compared to Chitosan 3/NO-5k (MBC 1000 μg/mL). The association of Chitosan 2/NO-5k and Chitosan 3/NO-5k with *P. aeruginosa* biofilm was evaluated using confocal microscope. As shown in FIG. 9A-F, biofilms exposed to Chitosan 2/NO-5k exhibited more intense red fluorescence compared to Chitosan 3/NO-5k, again confirming the enhanced association of the positively charged Chitosan 2/NO-5k with the bacteria.

7. Confocal Microscopy

*P. aeruginosa* was cultured in TSB to a concentration of ~1×10⁸ CFU/mL, collected via centrifugation (3645×g for 10 min), resuspended in sterile PBS, and adjusted to ~1×10⁶ CFU/mL. Aliquots of the bacteria solution were incubated in a glass bottom confocal dish for 1.5 h at 37° C. A Zeiss 510 Meta inverted laser scanning confocal microscope with a 543 nm HeNe excitation laser and a LP 585 nm filter was used to obtain fluorescence images of the rhodamine B isothiocyanate (RITC)-modified chitosan oligosaccharides. The bright field and fluorescence images were collected by a N.A. 1.2 C-apochromat water immersion lens with a 40× objective. Solutions of RITC-labeled NO-releasing chitosan oligosaccharides in PBS (1.5 mL) were added to the bacteria solution (1.5 mL) in the glass confocal dish to achieve a final concentration of 150 μg/mL. Images were collected every 2 min to characterize the association, if any, of the chitosan oligosaccharides with *P. aeruginosa* temporally. To observe the association of chitosan oligosaccharides with bacteria within biofilms, Established biofilms stained with syto 9 (10 μM) were incubated with RITC-labeled chitosan oligosaccharides (150 μg/mL in PBS) for 2.5 h. Prior to imaging, samples were rinsed with PBS (3×). A Zeiss 510 Meta inverted laser scanning confocal microscope with 488 nm Ar and 543 nm HeNe excitation lasers, and a BP 505-530 nm and LP 585 nm filters, respectively, was used to obtain all confocal images. Fluorescence images were collected with a 20× objective.

Figures 10A, 10B, 10C, 10D, 10E, 10F, 10G, 10H:
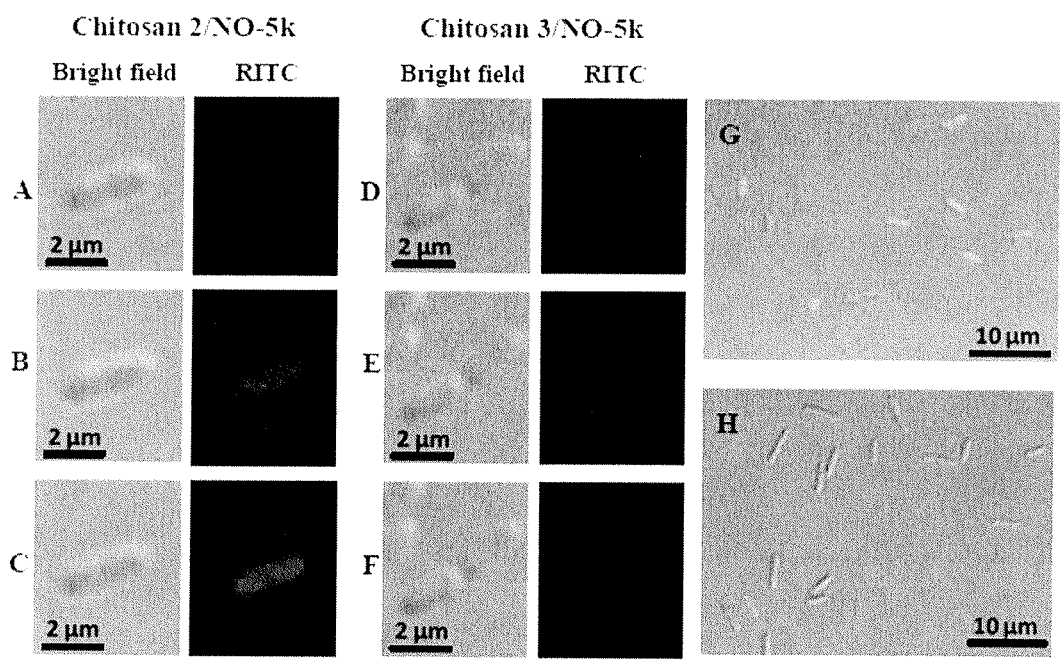
FIG. 10A-H depict Bright field and fluorescent images of RITC-modified Chitosan 2/NO-5k at A) 24, B) 28, C) 42 min and Chitosan 3/NO-5k at D) 82, E) 86, F) 110, H) 120 min (150 μg mL$^{-1}$) association with *P. aeruginosa*. Overlay images of *P. aeruginosa* incubated with G) Chitosan 2/NO-5k at 44 min and H) Chitosan 2/NO-5k at 120 min.

Confocal microscopy was utilized to compare the association kinetics of Chitosan 3/NO-5k and Chitosan 2/NO-5k with bacteria. Rhodamine B isothiocyanate (RITC)-labeled Chitosan 2/NO-5k and Chitosan 3/NO-5k were synthesized. Maghami (1988). The potential impact of RITC on chitosan-bacteria association was minimized by using small concentration of RITC (i.e., in 1:100 molar ratio to total primary amines). The degree of association of the NO-releasing chitosan oligosaccharides with bacteria was then followed by measuring red fluorescence surrounding the bacteria. Chitosan 2/NO-5k associated with the bacteria more rapidly (within 24 min) than Chitosan 3/NO-5k (86 min) (FIG. 10). The fluorescence from Chitosan 2/NO-5k at 42 min was significantly greater than that of Chitosan 3/NO-5k at 110 min, further demonstrating that Chitosan 3/NO-5k associated with the bacteria at a much slower rate due to the PEG (neutral) modification. Further inspection of Chitosan 2/NO-5k and Chitosan 3/NO-5k association with *P. aeruginosa* revealed enhanced bacteria association for Chitosan 2/NO-5k (FIG. 10-G, H).

Although chitosan molecular weight was not observed to play a significant role in planktonic killing, less effective bacteria killing was observed when using Chitosan 2/NO-10k, the largest chitosan oligosaccharides (600 μg/mL vs. 400 μg/mL for Chitosan 2/NO-10k and Chitosan 2/NO-2.5k) against biofilms. The efficient association of chitosan oligosaccharides with bacteria in biofilms is advantageous in view of previously reported NO-releasing polysaccharides which are insoluble under physiological conditions. All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A polyglucosamine comprising, at least one structural unit:

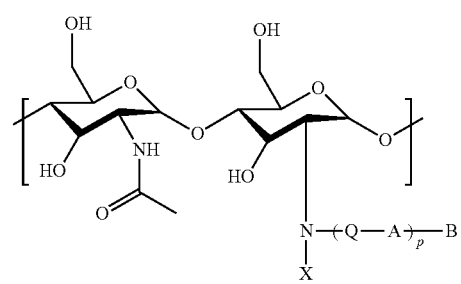

wherein,

Q is —(CR$_c$R$_d$)$_v$—;
    wherein R$_c$ and R$_d$, in each instance, are independently hydrogen or C$_{1-5}$ alkyl; and v is an integer from 2 to 6;

p is an integer from 1 to 10;

A is

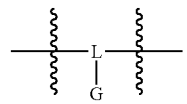

wherein, L is S, O or N; and

G, in each instance, is independently, hydrogen, or is taken together with

L to form a nitric oxide donor or is absent;

X is hydrogen, C$_{1-5}$ alkyl or is taken together with N to form a nitric oxide donor;

B is absent or is selected from the group consisting of hydrogen, hydroxyl, C$_{1-5}$ alkyl, or —Y—Z, wherein Y is a spacer and Z is a polymer or a terminus;

wherein the polyglucosamine comprises at least one nitric oxide donor selected from the group consisting of a diazeniumdiolate, nitrosothiol, a nitrosamine, a hydroxyl nitrosamine, a hydroxyl amine, a hydroxyurea, and combination thereof; and wherein G is taken together with L to form the at least one nitric oxide donor or X is taken together with N to form the at least one nitric oxide donor.

2. The polyglucosamine of claim 1, wherein said at least one nitric oxide donor is a diazeniumdiolate.

3. The polyglucosamine of claim 1, wherein B is hydrogen.

4. The polyglucosamine of claim 1, wherein B is —Y—Z.

5. The polyglucosamine of claim 4, wherein B is —Y—Z, wherein Z has the structure:

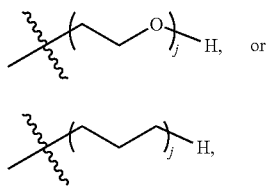

wherein j, in each instance, is an integer from 1 to 100.

6. The polyglucosamine of claim 4, wherein Y has the structure:

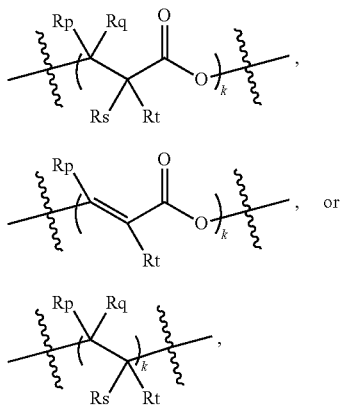

wherein,
$R_p$, $R_q$, $R_s$ and $R_t$, in each instance, are independently, hydrogen or hydroxyl; and
k is an integer from 1 to 20.

7. The polyglucosamine of claim 1, wherein
B is —Y—Z, wherein Z has the structure:

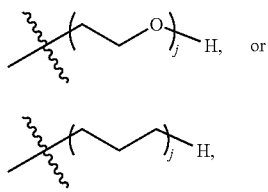

wherein j, in each instance, is an integer from 1 to 100.

8. The polyglucosamine of claim 7, wherein j is an integer from 1 to 50.

9. The polyglucosamine of claim 7, wherein j is an integer from 1 to 15.

10. The polyglucosamine of claim 1, wherein
A is

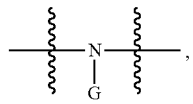

wherein G is hydrogen, or is taken together with N to form a nitric oxide donor or is absent; and
B is hydrogen.

11. The polyglucosamine of claim 10, wherein
X is hydrogen or is taken together with N to form a diazeniumdiolate; and
A is

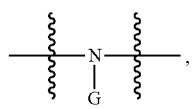

wherein G is hydrogen or is taken together with N to form a diazeniumdiolate.

12. The polyglucosamine of claim 1, comprising the structural unit:

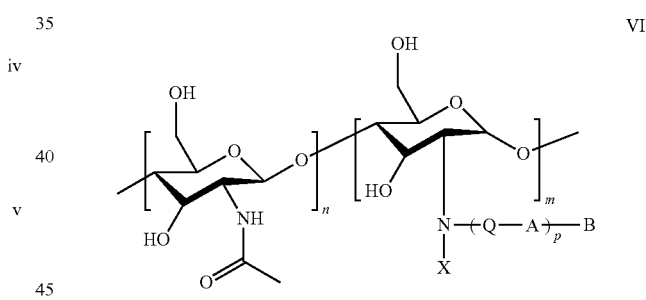

wherein,
m is an integer from 1 to 1,000, and
n is an integer from 1 to 1,000.

13. The polyglucosamine of claim 12, wherein m and n are each independently selected from an integer of 1 to 50.

14. The polyglucosamine of claim 13, wherein Y has the structure:

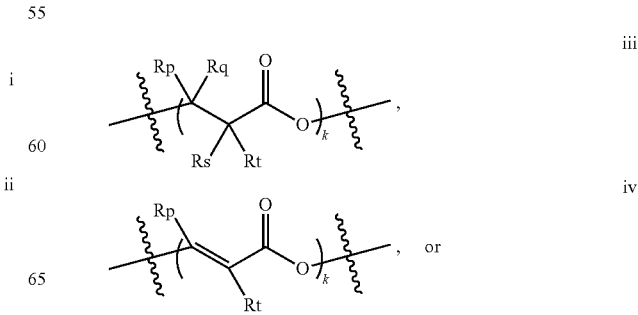

-continued

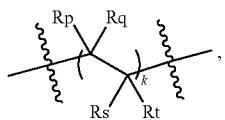

wherein, $R_p$, $R_q$, $R_s$ and $R_t$, in each instance, are independently, hydrogen or hydroxyl; and k is an integer from 1 to 20.

15. The polyglucosamine of claim 12, wherein m and n are each independently selected from an integer from 1 to 10.

16. The polyglucosamine of claim 12, comprising the structural unit:

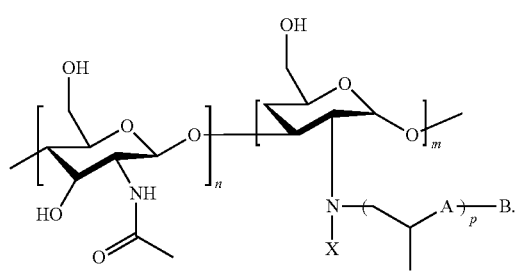

VII

17. The polyglucosamine of claim 12, wherein B is —Y—Z, wherein Z has the structure:

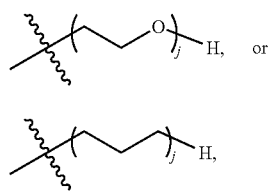

i ii wherein j, in each instance, is an integer from 1 to 100.

18. The polyglucosamine of claim 1, wherein A is N.

19. The polyglucosamine of claim 1, wherein A is S.

20. The polyglucosamine of claim 1, wherein $R_c$ and $R_d$, in each instance, are independently hydrogen or methyl; and v is 2.

21. The polyglucosamine of claim 1, wherein said polyglucosamine is water soluble.

22. The polyglucosamine of claim 1, wherein said polyglucosamine has a molecular weight from 100 to 20,000 g/mol.

23. The polyglucosamine of claim 1, wherein G is taken together with L to form said at least one nitric oxide donor.

24. The polyglucosamine of claim 1, wherein X is taken together with N to form said at least one nitric oxide donor.

25. The polyglucosamine of claim 24, wherein said at least one nitric oxide donor is a diazeniumdiolate.

26. The polyglucosamine of claim 24, wherein said at least one nitric oxide donor is a nitrosothiol.

27. The polyglucosamine of claim 1, comprising the structural unit:

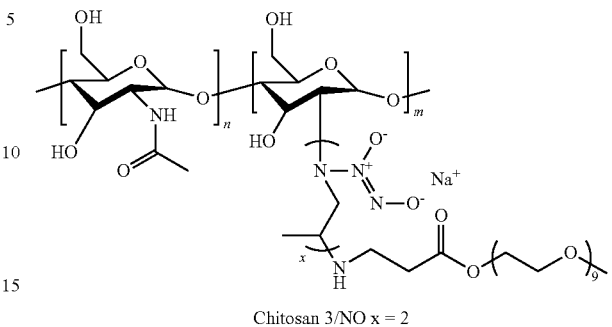

Chitosan 3/NO x = 2 wherein, m is an integer from 1 to 1,000, and n is an integer from 1 to 1,000.

28. The polyglucosamine of claim 1, comprising the structural unit:

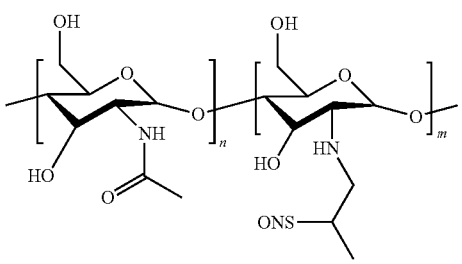

wherein, m is an integer from 1 to 1,000, and n is an integer from 1 to 1,000.

29. A polyglucosamine comprising:

at least one structural unit:

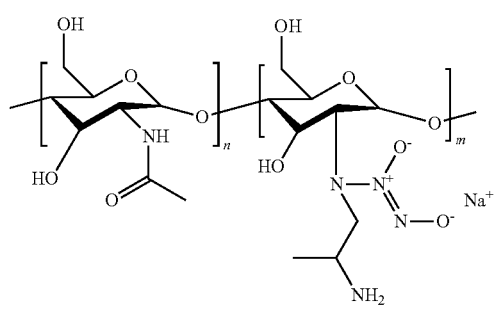

wherein, m is an integer from 1 to 1,000, and n is an integer from 1 to 1,000.

30. The polyglucosamine of claim 29, wherein m and n are each independently selected from an integer of 1 to 50.

31. A polyglucosamine comprising:
at least one structural unit:

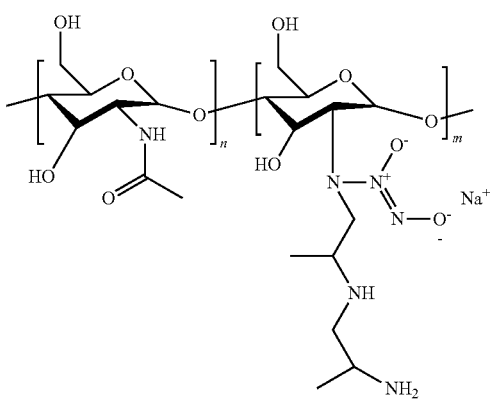

wherein,
m is an integer from 1 to 1,000, and
n is an integer from 1 to 1,000.

32. The polyglucosamine of claim 31, wherein m and n are each independently selected from an integer of 1 to 50.

33. A method of delivering nitric oxide to a subject, comprising:
administering an effective amount of said polyglucosamine of claim 1 to said subject.

34. A method of treating a disease state, comprising:
administering an effective amount of said polyglucosamine of claim 1 to a subject in need thereof, wherein said disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

35. The method of claim 34, wherein said disease state is cystic fibrosis.

36. A pharmaceutical formulation comprising:
i. said polyglucosamine of claim 1; and
ii. a pharmacuetically acceptable carrier.

37. The pharmaceutical formulation of claim 36, wherein said polyglucosamine is water-soluble.

* * * * *